US008639486B2

(12) United States Patent
Tavarekere et al.

(10) Patent No.: US 8,639,486 B2
(45) Date of Patent: Jan. 28, 2014

(54) **METHOD FOR IDENTIFYING INHIBITORS OF *STAPHYLOCOCCUS AUREUS***

(75) Inventors: Girish S Tavarekere, Bangalore (IN); Gopal Balasubramanian, Bangalore (IN)

(73) Assignee: Indian Institute of Science, Bangalore (IN)

( * ) Notice: Subject to any disclaimer, the term of this patent is extended or adjusted under 35 U.S.C. 154(b) by 294 days.

(21) Appl. No.: 12/840,925

(22) Filed: Jul. 21, 2010

(65) Prior Publication Data

US 2011/0300561 A1 Dec. 8, 2011

(30) Foreign Application Priority Data

Jun. 7, 2010 (IN) ........................... 1572/CHE/2010

(51) Int. Cl.
*G06G 7/58* (2006.01)
*G01N 33/48* (2006.01)

(52) U.S. Cl.
USPC ............................................... 703/11; 702/19

(58) Field of Classification Search
None
See application file for complete search history.

(56) References Cited

U.S. PATENT DOCUMENTS

| | | | | |
|---|---|---|---|---|
| 4,522,811 A | | 6/1985 | Eppstein et al. | |
| 5,463,564 A | * | 10/1995 | Agrafiotis et al. | 700/268 |

OTHER PUBLICATIONS

Atkinson, S.C., et al., "Crystallization and preliminary X-ray analysis of dihydrodipicolinate synthase from *Clostridium botulinum* in the presence of its substrate pyruvate," Acta Crystallogr Sect F Struct Biol Cryst Commun. Mar. 1, 2009;65(Pt 3):253-255.

Burgess, B.R., et al., "Purification, crystallization and preliminary X-ray diffraction studies to near-atomic resolution of dihydrodipicolinate synthase from methicillin-resistant *Staphylococcus aureus*," Acta Crystallogr Sect F Struct Biol Cryst Commun. Jul. 1, 2008;64(Pt 7):659-661.

Chevrier, B., et al., "The Structure of the Aeromonas proteolytica Aminopeptidase Complexed with a Hydroxamate Inhibitor," European Journal of Biochemistry, vol. 237, Issue 2, pp. 393-398, 1996.

Coulter, C. V., et al., "*Escherichia coli* dihydrodipicolinate synthase and dihydrodipicolinate reductase: kinatic and inhibition studies of two putative herbicide targets," Pestic. Sci., vol. 55, 1999, pp. 887-895.

Dobson, R.C.J., et al., "The crystal structures of native and (S)-lysine-bound dihydrodipicolinate synthase from *Escherichia coli* with improved resolution show new features of biological significance," Acta Crystallogr D Biol Crystallogr. Aug. 2005;61(Pt 8):1116-1124.

Dobson, R.C.J., et al., "The purification, crystallization and preliminary X-ray diffraction analysis of dihydrodipicolinate synthase from *Clostridium botulinum*," Acta Crystallographica Section F, vol. 64, Issue 3, pp. 206-208, 2008.

Kapoor, S., et al., "Inhibition of a Protein Tyrosine Phosphatase Using Mesoporous Oxides," J. Phys. Chem. B, 2010, 114 (9), pp. 3117-3121.

Kefala, G., "Cloning, expression, purification, crystallization and preliminary X-ray diffraction analysis of DapA (Rv2753c) from *Mycobacterium tuberculosis*," Acta crystallographica. Section F, Structural biology and crystallization communications 2006;62(Pt 11):1116-1119.

Lindner, H.A., et al., "Essential Roles of Zinc Ligation and Enzyme Dimerization for Catalysis in the Aminoacylase-1/M20 Family," Journal of Biological Chemistry, 278, 44496-44504.

Lundgren, S., et al., "Crystal structures of yeast beta-alanine synthase complexes reveal the mode of substrate binding and large scale domain closure movements," J Biol Chem. Dec. 7, 2007;282(49):36037-36047.

Nocek, BP., et al., "Structural basis for catalysis by the mono- and dimetalated forms of the dapE-encoded N-succinyl-L,L-diaminopimelic acid desuccinylase," J Mol Biol., Apr. 2, 2010;397(3):617-626.

Voss., J.E., et al., "Expression, purification, crystallization and preliminary X-ray diffraction analysis of dihydrodipicolinate synthase from *Bacillus anthracis* in the presence of pyruvate," Acta Crystallogr Sect F Struct Biol Cryst Commun., Feb. 1, 2009;65(Pt 2):188-191.

Zauhar, R., "Structure-Activity Relationship and Drug Design," Remington:The Science and Practice of Pharmacy, 21st Edition, Lippincott Williams & Wilkins, University of the Sciences in Philadelphia, May 2005, pp. 468-478.

Addlagatta, A., et al., "Structure of aminopeptidase N from *Escherichia coli* suggests a compartmentalized, gated active site," Proc. Natl. Acad. Sci., 2006, vol. 103, No. 36, pp. 13339-13344.

Antane, S., et al., "Pulvinones as Bacterial Cell Wall Biosynthesis Inhibitors," Bioorganic & Medicinal Chemistry Letters, vol. 16, Issue 1, pp. 176-180.

Bebrone, C., et al., "Metallo-beta-lactamases (classification, activity, genetic organization, structure, zinc coordination) and their superfamily," Biochemical Pharmacology, vol. 74, Issue 12, pp. 1686-1701, 2007.

Biagini, A., et al., "Sequence analysis of the aminoacylase-1 family. A new proposed signature for metalloexopeptidases," Comp Biochem Physiol B Biochem Mol Biol. Mar. 2001;128(3):469-481.

Blickling, S., et al., "Structure of dihydrodipicolinate synthase of *Nicotiana sylvestris* reveals novel quaternary structure," J Mol Biol. Dec. 12, 1997;274(4):608-621.

Born, T. L., et al., "Structure/function studies on enzymes in the diaminopimelate pathway of bacterial cell wall synthesis." Current Opinion in Chemical Biology, vol. 3, Issue 5, 1999, pp. 607-613.

(Continued)

*Primary Examiner* — Eric S Dejong
(74) *Attorney, Agent, or Firm* — Foley & Lardner LLP

(57) ABSTRACT

Provided are methods for identifying and/or designing inhibitors of *Staphylococcus aureus* biological activity. Also provided is a computer readable medium encoded with instructions executable by a CPU for performing the functions of identifying or designing inhibitors of *Staphylococcus aureus* biological activity, and a system comprising the computer readable medium and a CPU. Also provided are compounds identified and/or designed by the methods, methods of treatment including the compounds, methods of inhibiting *S. aureus* using the compounds, medicaments including the compounds for use in the treatment of *S. aureus* infection, or conditions related to *S. aureus* infection, and pharmaceutical compositions including the compounds. Methods for identifying a bacterial cell that is resistant to methicillin are also provided.

8 Claims, 16 Drawing Sheets

(56) References Cited

OTHER PUBLICATIONS

Collaborative Computational Project, No. 4, "The CCP4 suite: programs for protein crystallography," Acta Cryst. (1994). D50, 760-763.

Dobson, R. C.J., et al., "Specificity versus catalytic potency: The role of threonine 44 in *Escherichia coli* dihydrodipicolinate synthase mediated catalysis," Biochimie. Aug. 2009;91(8):1036-1044.

Dobson, R., C.J., et al., "The crystal structure of three site-directed mutants of *Escherichia coli* dihydrodipicolinate synthase: further evidence for a catalytic triad," J Mol Biol. Apr. 23, 2004;338(2):329-339.

Doi, E., et al., "Modified colorimetric ninhydrin methods for peptidase assay," Anal Biochem. Nov. 15, 1981;118(1):173-184.

Domigan, L.J., et al., "Characterisation of dihydrodipicolinate synthase (DHDPS) from *Bacillus anthracis*," Biochim Biophys Acta, Oct. 2009;1794(10):1510-1516.

Gillner, D., et al., "Inhibitors of bacterial N-succinyl-L,L-diaminopimelic acid desuccinylase (DapE) and demonstration of in vitro antimicrobial activity," Bioorganic & Medicinal Chemistry Letters 19 (2009) 6350-6352.

Girish, T. S., et al., "Structural and functional characterization of *Staphylococcus aureus* dihydrodipicolinate synthase," FEBS Letters, vol. 582, Issue 19, 2008, pp. 2923-2930.

Greenblatt, H. M., et al., "*Streptomyces griseus* aminopeptidase: X-ray crystallographic structure at 1.75 A resolution," J Mol Biol. Feb. 7, 1997;265(5):620-636.

Hutton, C. A., et al., "Inhibition of lysine biosynthesis: an evolving antibiotic strategy," Mol. Biosyst., 2007, 3, pp. 458-465.

Jozic, D., et al., "Crystal structure of the dinuclear zinc aminopeptidase PepV from *Lactobacillus delbrueckii* unravels its preference for dipeptides," Structure. Aug. 2002;10(8):1097-1106.

Kefala, G., et al., "Crystal structure and kinetic study of dihydrodipicolinate synthase from *Mycobacterium tuberculosis*," Biochem J. Apr. 15, 2008;411(2):351-360.

Maurice, F., et al., "Enzyme structural plasticity and the emergence of broad-spectrum antibiotic resistance," EMBO Reports, 9, 4, 2008, pp. 344-348.

Munih, P., et al., "X-ray crystallographic characterization of the Co(II)-substituted Tris-bound form of the aminopeptidase from *Aeromonas proteolytica*," Journal of Inorganic Biochemistry 101 (2007) 1099-1107.

Mwangi, M. M., et al., "Tracking the in vivo evolution of multidrug resistance in *Staphylococcus aureus* by whole-genome sequencing," Proc. Natl. Acad. Sci., 2007, vol. 104, No. 22, pp. 9451-9456.

Noda, M., et al., "Structural Evidence that Alanine Racemace from a D-Cycloserine-producing Microorganism Exhibits Resistance to Its Own Product," J. Biol. Chem., vol. 279, No. 44, 2004, pp. 46153-46161.

Payne, D. J., et al., "Drugs for bad bugs: confronting the challenges of antibacterial discovery," Nature Reviews Drug Discovery, 2007, vol. 6, pp. 29-40.

Rice, E. A., et al., "Characterization and crystal structure of lysine insensitive *Corynebacterium glutamicum* dihydrodipicolinate synthase (cDHDPS) protein," Arch Biochem Biophys. Dec. 15, 2008;480(2):111-121.

Rowsell, S., et al., "Crystal structure of carboxypeptidase G2, a bacterial enzyme with applications in cancer therapy," Structure, vol. 5, Issue 3, 337-347, Mar. 15, 1997.

Scapin, G., et al., "Enzymology of bacterial lysine biosynthesis," Advances in Enzymology and Related Areas of Molecular Biology, 1998, 72: 279-324.

Storoni, L.C., et al., "Likelihood-enhanced fast rotation functions," Acta Crystallogr D Biol Crystallogr. Mar. 2004;60(Pt 3):432-438.

Walsh, C., et al., "Molecular mechanisms that confer antibacterial drug resistance," Nature, 2000, 406: 775-781.

Zhou, Y., et al., "Penicillin-Binding Proteins and Cell Wall Composition in β-Lactam-Sensitive and -Resistant Strains of *Staphylococcus sciuri*," Journal of Bacteriology, Jan. 2008, pp. 508-514, vol. 190, No. 2.

Isabell Staub et al., "β-Lactam Probes As Selective Chemical-Proteomic Tools for the Identification and Functional Characterization of Resistance Associated Enzymes in MRSA," J. Am. Chem. Soc., vol. 131, No. 17, American Chemical Society, pp. 6271-6276 (2009).

\* cited by examiner

FIGURE 1
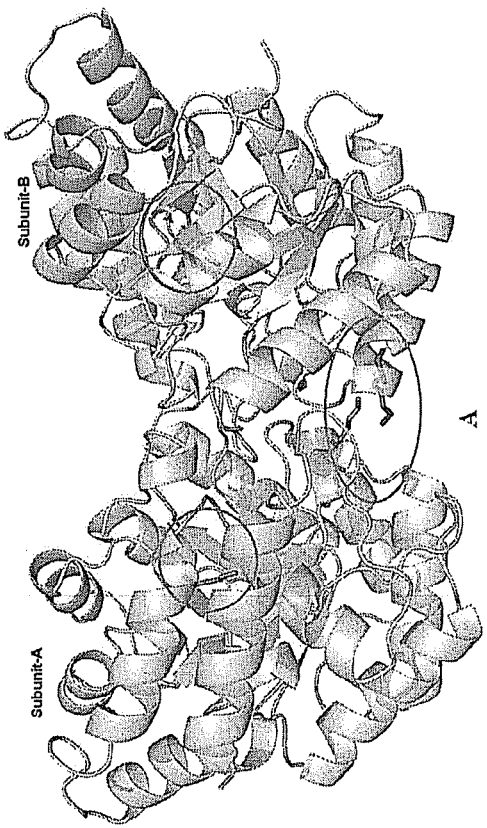
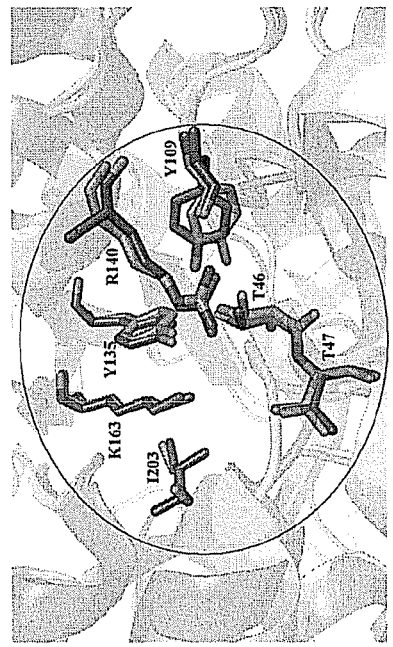
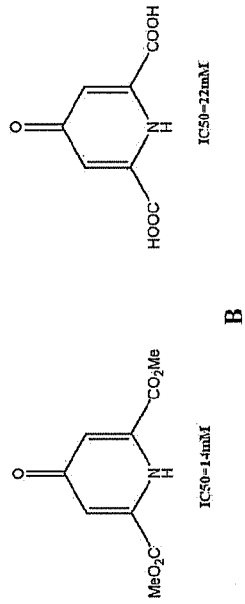
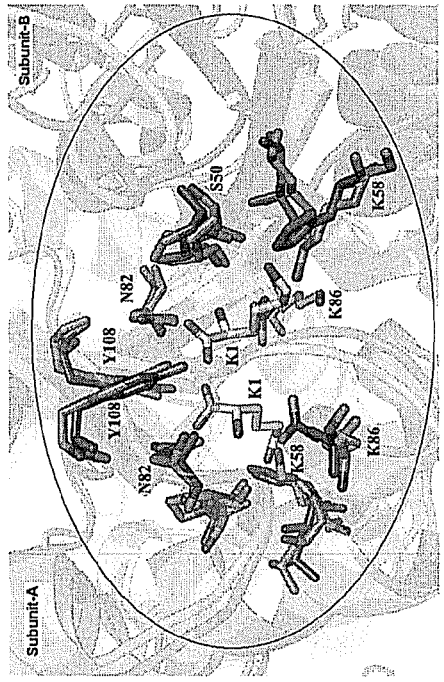

Figure 9: Lysine Biosynthesis Pathway

Figure 13

(A) DapA Amino Acid Sequence (SEQ ID NO: 1)

```
MTHLFEGVGV ALTTPFTNNK VNIEALKTHV NFLLENNAQA IIVNGTTAES PTLTTDEKER
ILKTVIDLVD KRVPVIAGTG TNDTEKSIQA SIQAKALGAD AIMLITPYYN KTNQRGLVKH
FEAIADAVKL PVVLYNVPSR TNMTIEPETV EILSQHPYIV ALKDATNDFE YLEEVKKRID
TNSFALYSGN DDNVVEYYQR GGQGVISVIA NVIPKEFQAL YDAQQSGLDI QDQFKPIGTL
LSALSVDINP IPIKALTSYL GFGNYELRLP LVSLEDTDTK VLRETYDTFK AGENE
```

(B) DapE Amino Acid Sequence (SEQ ID NO: 2)

```
MWKEKVQQYE DQIINDLKGL LAIESVRDDA KASEDAPVGP GPRKALDYMY EIAHRDGFTT
HDVDHIAGRI EAGKGNDVLG ILCHVDVVPA GDGWDSNPFE PVVTEDAIIA RGTLDDKGPT
IAAYYAIKIL EDMNVDWKKR IHMIIGTDEE SDWKCTDRYF KTEEMPTLGF APDAEFPCIH
GEKGITTFDL VQNKLTEDQD EPDYELITFK SGERYNMVPD HAEARVLVKE NMTDVIQDFE
YFLEQNHLQG DSTVDSGILV LTVEGKAVHG MDPSIGVNAG LYLLKFLASL NLDNNAQAFV
AFSNRYLFNS DFGEKMGMKF HTDVMGDVTT NIGVITYDNE NAGLFGINLR YPEGFEFEKA
MDRFANEIQQ YGFEVKLGKV QPPHYVDKND PFVQKLVTAY RNQTNDMTEP YTIGGGTYAR
NLDKGVAFGA MFSDSEDLMH QKNEYITKKQ LFNATSIYLE AIYSLCVEE
```

METHOD FOR IDENTIFYING INHIBITORS OF *STAPHYLOCOCCUS AUREUS*

CROSS-REFERENCE TO RELATED APPLICATIONS

This application claims the benefit of priority of Indian Patent Application No. 1572/CHE/2010, filed Jun. 7, 2010, which is hereby incorporated by reference in its entirety.

DESCRIPTION OF THE ELECTRONIC COMPUTER READABLE FORMS

Submitted herewith are Tables S1, S2, and S3 each formatted as ASCII text files. The file containing Table S1 is entitled "dapE_open.txt," created on Jul. 21, 2010, and is 553,380 bytes in size. The file containing Table S2 is entitled "dapE_closed.txt," created on Jul. 21, 2010, and is 303,419 bytes in size. The file containing Table S3 is entitled "dapE_Mut350A.txt," created on Jul. 21, 2010, and is 569,823 bytes in size.

LENGTHY TABLES

The patent contains a lengthy table section. A copy of the table is available in electronic form from the USPTO web site (http://seqdata.uspto.gov/?pageRequest=docDetail&DocID=US08639486B2). An electronic copy of the table will also be available from the USPTO upon request and payment of the fee set forth in 37 CFR 1.19(b)(3).

The disclosure of Tables S1, S2, S3, submitted as electronic documents, as described above, form part of this patent application and are hereby expressly incorporated by reference.

Also included in computer readable form is a sequence listing formatted as an ASCII text file entitled "Sequence_Listing.txt," created on Jul. 21, 2010, and is 9,535 bytes in size. The sequence listing is also incorporated by reference.

BACKGROUND

A number of respiratory infections are known to be caused by microbes such as *S. pneumoniae, S. aureus, C. pneumoniae, H. influenzae, M. catarrhalis, M. pneumoniae,* and *L. pneumophila*. Many of these microbes are able to develop rapid resistance to commonly used antibiotic agents such as penicillin, oxacillin, flucloxacillin, and methicillin. In particular *S. aureus* exhibits a robust ability to acquire resistance to antibiotic agents (whether by acquisition of resistance genes or developing novel resistance mechanisms). One *S. aureus* strain, for example, has developed a broad-based resistance to common "front line" antibiotics (all β-lactams) as well as to antibiotics of "last resort" such as Vancomycin. This strain has been termed "MRSA" (methicillin-resistant *Staphylococcus aureus*) and presents a particular public health concern because it is not only involved with mild skin and soft tissue infections (e.g., folliculitis), but also can cause more serious respiratory infections (e.g., pneumonia) as well as sepsis, osteomyelitis, septic arthritis, endocarditis, and toxic shock syndrome. *S. aureus* is also a leading cause of primary infections originating in hospitals.

Several broad-spectrum antibiotics are currently used to treat of *S. aureus* infections. These antibiotics commonly target any number of biochemical pathways including cell-wall biosynthesis (e.g., β-lactams and vancomycin), bacterial protein synthesis (e.g., erythromycins, tetracyclins, aminoglycosides and oxazolidinones) and bacterial DNA replication and repair (e.g., fluoroquinolones). As microbial strains have developed resistance to a number of commonly used antibiotics, the efficacy of these known active agents has decreased severely.

Drug resistant *S. aureus* strains include modifications in surface proteins that promote colonization of host tissues, biochemical variations that enhance survival in phagocytes and evasion of the host immune system, enhanced release of toxins that lyse eukaryotic cell membranes and active efflux of antibiotics coupled with mutation events in target molecules that abrogate the action of drugs, among others.

Accordingly the continued development and discovery of compounds that can inhibit biological activity of infective microbial organisms, such as methicillin-resistant *S. aureus*, will aid providing more successful outcomes for subjects with microbial infections and conditions related to such infections. Further, continued development of methods for accurately identifying infective microbial organisms will more effectively address this public health issue.

SUMMARY

Aspects provide methods for identifying a candidate inhibitor that binds to a site of *Staphylococcus aureus* dihydrodipicolinate synthase (DapA) or a homologue or active fragment thereof, comprising:
   obtaining the structure coordinates of amino acids of DapA or a homologue or active fragment thereof;
   generating a three-dimensional model of DapA or a homologue or active fragment thereof using the structure coordinates of the amino acids from DapA, wherein the model comprises a root mean square deviation from backbone atoms of said amino acids of not more than ±1.0 Å;
   determining a binding site of DapA or a homologue or active fragment thereof from the three-dimensional model; and
   performing a computer fitting analysis to identify the candidate inhibitor that interacts with the binding site.

Aspects provide methods for identifying a candidate inhibitor that binds to a site of *Staphylococcus aureus* dihydrodipicolinate synthase (DapA) or a homologue or active fragment thereof, comprising:
   obtaining the structure coordinates of amino acids of DapA or homologue or active fragment thereof;
   generating a three-dimensional model of DapA or homologue or active fragment thereof using the structure coordinates of the amino acids from DapA, wherein the model comprises a root mean square deviation from backbone atoms of said amino acids of not more than ±1.0 Å;

determining a binding site of DapA or homologue or active fragment thereof from the three-dimensional model;

performing a computer fitting analysis to identify the candidate inhibitor that interacts with the binding site; and contacting the identified candidate inhibitor with DapA or homologue or active fragment thereof under conditions that allow for the determination of the effect of the inhibitor on S. aureus biological activity.

Aspects provide methods for identifying a candidate inhibitor that binds to a site of Staphylococcus aureus N-Succinyl-L,L-DAP Desuccinylase (DapE) or a homologue or active fragment thereof, comprising:

obtaining the structure coordinates of amino acids of DapE or homologue or active fragment thereof;
  generating a three-dimensional model of DapE or homologue or active fragment thereof using the structure coordinates of the amino acids from DapE, wherein the model comprises a root mean square deviation from backbone atoms of said amino acids of not more than ±1.0 Å;
  determining a binding site of DapE or homologue thereof from the three-dimensional model; and
  performing a computer fitting analysis to identify the candidate inhibitor that interacts with the binding site.

Aspects provide methods for identifying a candidate inhibitor that binds to a site of Staphylococcus aureus N-Succinyl-L,L-DAP Desuccinylase (DapE) or a homologue or active fragment thereof, comprising:

obtaining the structure coordinates of amino acids of DapE or homologue or active fragment thereof;
  generating a three-dimensional model of DapE or homologue or active fragment thereof using the structure coordinates of the amino acids from DapE, wherein the model comprises a root mean square deviation from backbone atoms of said amino acids of not more than ±1.0 Å;
  determining a binding site of DapE or homologue or active fragment thereof from the three-dimensional model;
  performing a computer fitting analysis to identify the candidate inhibitor that interacts with the binding site; and
  contacting the identified candidate inhibitor with DapE or homologue or active fragment thereof under conditions that allow for determination the effect of the inhibitor on S. aureus biological activity.

Aspects provide computer readable media having stored therein instructions executable by a computing device to cause the computing device to perform the functions of:

obtaining structure coordinates of amino acids of DapA or DapE;
  obtaining structure data for the one or more candidate inhibitors;
  fitting the structure data for the one or more candidate inhibitors to the structure coordinates of amino acids of DapA or DapE;
  generating a fit value for the one or more candidate inhibitors from fitting the structure data;
  comparing the fit value with a predetermined value;
  based on the comparison, determining whether the fit value for the one or more candidate inhibitors is within a predetermined value;
  classifying the fit value for the one or more candidate inhibitors as either a "good" fit if the fit value is within the predetermined value or a "bad" fit if the fit value is not within the predetermined value; and
  selecting the candidate inhibitors classified as a "good" fit for further evaluation of inhibitor activity against S. aureus; and discarding the candidate inhibitors classified as a "bad" fit.

Aspects provide methods for identifying a bacterial cell that is resistant to methicillin (MRSA) comprising: providing a bacterial cell; generating a conjugate molecule, wherein the conjugate molecule comprises a compound that binds to N-Succinyl-L,L-DAP desuccinylase (DapE) linked to a detectable signaling molecule; contacting the bacterial cell with the conjugate molecule under conditions that allow for binding of the conjugate molecule with DapE; and detecting the presence or absence of conjugate molecule associated with the bacterial cell, wherein the bacterial cell is identified as methicillin-resistant when an amount of conjugate molecule associated with the bacterial cell is detected.

Aspects provide systems configured to identify one or more candidate inhibitors of Staphylococcus aureus biological activity comprising:

a computing device;
  a computer readable medium having stored therein instructions executable by the computing device to cause the computing device to perform the functions of:
    obtaining structure coordinates of amino acids of DapA or DapE;
    obtaining structure data for the one or more candidate inhibitors;
    fitting the structure data for the one or more candidate inhibitors to the structure coordinates of amino acids of DapA or DapE;
    generating a fit value for the one or more candidate inhibitors from fitting the structure data;
    comparing the fit value with a predetermined value;
    based on the comparison, determining whether the fit value for the one or more candidate inhibitors is within a predetermined value;
    classifying the fit value for the one or more candidate inhibitors as either a "good" fit if the fit value is within the predetermined value or a "bad" fit if the fit value is not within the predetermined value; and
    selecting the candidate inhibitors classified as a "good" fit for further evaluation of inhibitor activity against S. aureus; and discarding the candidate inhibitors classified as a "bad" fit; and
  a graphical user interface display.

Aspects provide methods for designing a candidate inhibitor that binds to a site of Staphylococcus aureus dihydrodipicolinate synthase (DapA) or a homologue or active fragment thereof, comprising:

obtaining the structure coordinates of amino acids of DapA or a homologue or active fragment thereof;
  generating a three-dimensional model of DapA or a homologue or active fragment thereof using the structure coordinates of the amino acids from DapA, wherein the model comprises a root mean square deviation from backbone atoms of said amino acids of not more than ±1.0 Å;
  determining a binding site of DapA or a homologue or active fragment thereof from the three-dimensional model; and
  performing a computer fitting analysis to identify the candidate inhibitor that interacts with the binding site;

wherein the fitting analysis of the interaction between the candidate inhibitor and the binding site predicts that DapA activity will be inhibited.

Aspects provide methods for designing a candidate inhibitor that binds to a site of *Staphylococcus aureus* N-Succinyl-L,L-DAP Desuccinylase (DapE) or a homologue or active fragment thereof, comprising:

obtaining the structure coordinates of amino acids of DapE or a homologue or active fragment thereof;

generating a three-dimensional model of DapE or a homologue or active fragment thereof using the structure coordinates of the amino acids from DapE, wherein the model comprises a root mean square deviation from backbone atoms of said amino acids of not more than ±1.0 Å;

determining a binding site of DapE or a homologue or active fragment thereof from the three-dimensional model; and performing a computer fitting analysis to identify the candidate inhibitor that interacts with the binding site;

wherein the fitting analysis of the interaction between the candidate inhibitor and the binding site predicts that DapE activity will be inhibited.

Aspects provide compounds that inhibit the biological activity of *S. aureus*, which have been identified by the methods described herein.

Aspects provide pharmaceutical compositions comprising compounds that inhibit the biological activity of *S. aureus*, which have been identified by the methods described herein, in a pharmaceutically acceptable formulation.

Aspects provide methods of treating *S. aureus* infection a subject comprising administering to a subject in need of treatment at least one compound that inhibit the biological activity of *S. aureus* that has been identified by the methods described herein.

Aspects provide medicaments and methods for the preparation of medicaments comprising compounds that inhibit the biological activity of *S. aureus*, which have been identified by the methods described herein, for use in the treatment of *S. aureus* infection or conditions associated with *S. aureus* infection.

Aspects provide methods of inhibiting *S. aureus* biological activity comprising contacting a *S. aureus* cell with one or more compounds that inhibit the biological activity of *S. aureus*, which have been identified by the methods described herein.

Additional aspects of the application and various embodiments of these aspects will be apparent to one of skill in the art in light of the following detailed description.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 1 (A) depicts a structure of *S. aureus* DapA showing the dimeric arrangement of subunits and the location of the site mediating feedback inhibition region; (B) depicts an overlay fit of amino acid residues at the active site of *S. aureus* DapA (light gray) and *E. coli* DapA (dark gray), along with the structures of two *E. coli* DapA inhibitors; (C) depicts an overlay fit of amino acid residues at the lysine (Lys) binding pocket of *S. aureus* DapA and *E. coli* DapA.

FIG. 13 (A) depicts the amino acid sequence for DapA (SEQ ID NO:1) as described in Girish, et al., *FEBS Lett.*, 582(19):2923-2930 (2008), MMDB ID: 66050; PDB IDs: 3DI0 (native), 3DI1 (pyruvate complex). (B) depicts the amino acid sequence for DapE (SEQ ID NO:2) as described in GenBank Accession YP_186634; PDB IDs: 3KHX (open form), 3KHZ (R350A mutant), 3KI9 (closed form).

DETAILED DESCRIPTION

Figure 2:
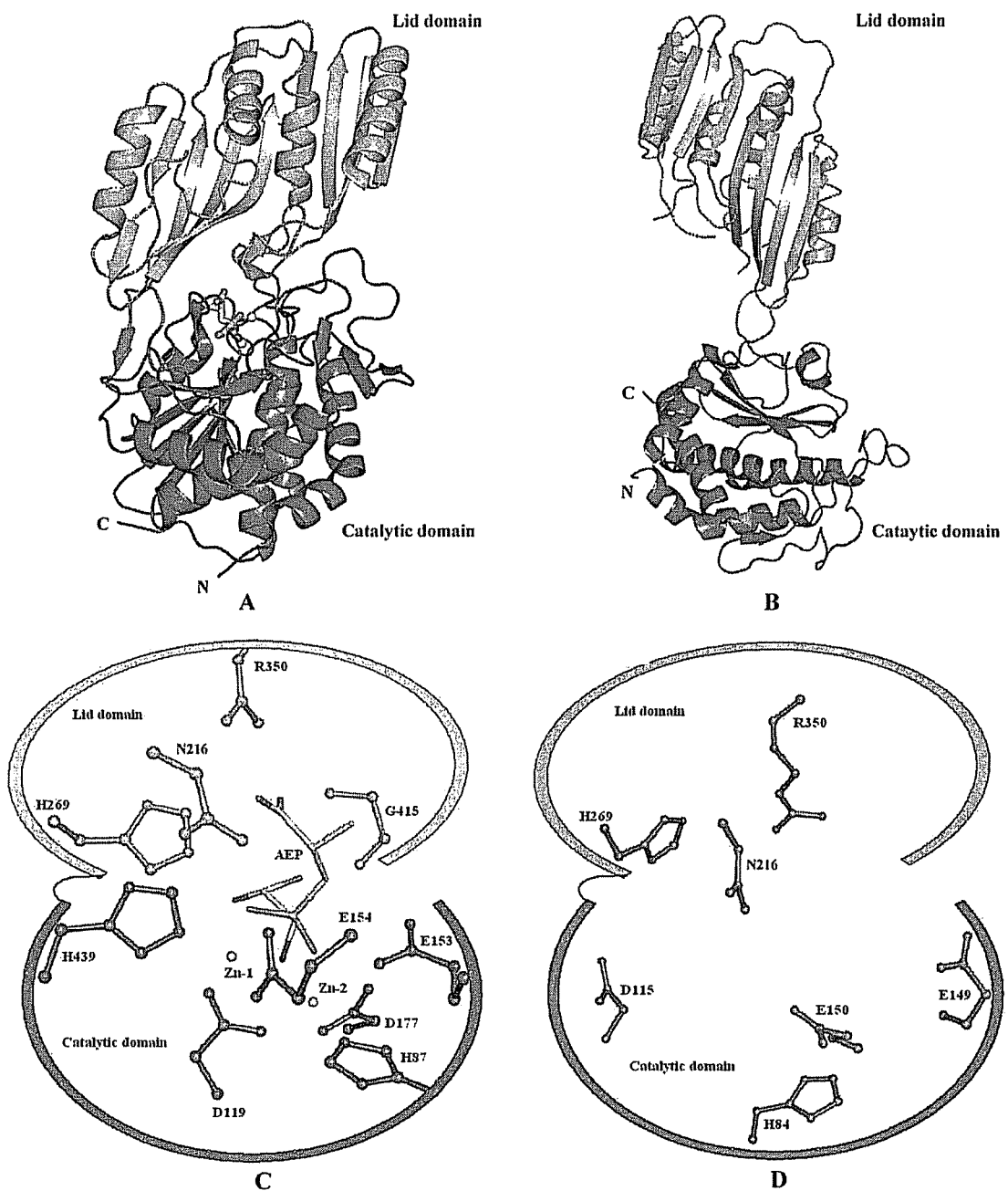
FIG. 2(A) depicts a structure of the dinuclear zinc aminopeptidase, pepV; (B) depicts a structure of *S. aureus* N-Succinyl-L,L-DAP Desuccinylase (DapE); (C) depicts the general structure of the active site of pepV, including the substrate (AEP) and amino acid ligands that form the dinuclear Zn site and that interact with the AEP substrate; (D) depicts the general structure of the active site of DapE and illustrates that active sites of pepV and DapE have similar structural elements, including distinct catalytic and lid domains.

In a broad sense, the disclosure provides diagnostic and therapeutic methods, and computer readable media and systems related thereto, as well as compounds and compositions that all relate to identifying the presence of and/or inhibiting the biological activity of *Staphylococcus aureus*. Aspects relate to the inhibition of, and/or the identification or design of inhibitors of *S. aureus* biochemical pathways that involve dihydrodipicolinate synthase (DapA) or N-Succinyl-L,L-DAP Desuccinylase (DapE), or both. Aspects also relate to identifying methicillin-resistant *S. aureus* (MRSA) bacterial cells that involve detecting the presence of N-Succinyl-L,L-DAP Desuccinylase (DapE) by contacting the bacteria with a conjugate molecule that includes a compound that binds to N-succinyl-L,L-DAP desuccinylase (DapE) linked to a detectable signaling molecule. Targeting the *S. aureus* DapA enzyme or DapE enzyme, or both, provides effective methods, compounds, and systems that are useful in the treatment of bacterial infection and identification of methicillin resistant bacteria, such as MRSA.

The term "*Staphylococcus aureus*" or "*S. aureus*" as used herein, without further description, relates to any strain of the Gram-positive bacteria classified as *Staphylococcus aureus*, and which have been associated with a number of infections, including pneumonia, osteomyelitis, arthritis, endocarditis, sepsis and toxic shock syndrome, as well as cause less severe infections of the skin and soft tissues.

The term "methicillin-resistant *Staphylococcus aureus*" or "MRSA" as used herein includes strains of *Staphylococcus aureus* that are resistant to methicillin and can also broadly relate to Gram-positive bacteria strains (e.g., beta-lactamase-producing bacteria) that are resistant to antibiotics falling within the general classification of penicillins. Methicillin is the common name for (2S,5R,6R)-6-[(2,6-dimethoxybenzoyl)amino]-3,3-dimethyl-7-oxo-4-thia-1-azabicyclo[3.2.0]heptane-2-carboxylic acid, which is a narrow spectrum beta-lactam antibiotic that has been used to treat infections caused by susceptible Gram-positive bacteria (e.g., including *Staphylococcus aureus*).

The term "dihydrodipicolinate synthase," "DHDPS," or "DapA" as used herein means an enzyme involved in the biosynthesis of lysine that (under appropriate conditions) catalyzes the condensation of pyruvate and aspartate semialdehyde to form dihydrodipicolinate. The term can include various DapA homologues, orthologs, variants, and fragments that can catalyze the synthesis of dihydrodipicolinate from pyruvate and aspartate semialdehyde. Non-limiting examples of DapA are described herein for purposes of illustrative embodiments (for example, *Staphylococcus aureus* DapA as disclosed in SEQ ID NO: 1, FIG. 13(A); See, Girish, et al. *FEBS Lett.*, 582(19): 2923-2930 (2008); MMDB ID: 66050; PDB ID: 3DI0). Several dihydrodipicolinate synthases have been have been biochemically and structurally characterized such as, for example, those described in the following references (each of which is incorporated by reference herein): (A) Domigan L. J., et al., *Biochim Biophys Acta*, 2009 October; 1794(10):1510-6. Epub 2009 Jul. 10; (B) Dobson et al., *Acta Crystallogr Sect F Struct Biol Cryst Commun*. (2008 Mar. 1); 64(Pt 3):206-208; (C) Voss J. E., et al., *Acta Crystallogr Sect F Struct Biol Cryst Commun*. (2009 Feb. 1); 65(Pt 2):188-91. Epub 2009 Jan. 31; (D) Burgess B. R. et al., *Acta Crystallogr Sect F Struct Biol Cryst Commun*. (2008 Jul. 1); 64(Pt 7):659-61. Epub 2008 Jun. 28; (E) Atkinson S. C., et al., *Acta Crystallogr Sect F Struct Biol Cryst Commun*. (2009 Mar. 1); 65(Pt 3):253-5. Epub 2009 Feb. 14; (F) Rice E. A., et al., *Arch Biochem Biophys*. (2008, Dec. 15); 480(2):111-21. Epub 2008 Oct. 7; (G) Dobson R. C., et al., *Biochimie*. (2009 August); 91(8):1036-44. Epub 2009 Jun. 6; (H) Dobson R. C., et al., *Acta Crystallogr D Biol Crystallogr*. (2005 August); 61(Pt 8):1116-24. Epub 2005 Jul. 20; (I) Dobson R. C., et al., *J Mol Biol*. (2004 Apr. 23); 338(2):329-39; (J) Kefala G., et al., *Biochem J*. (2008 Apr. 15); 411(2):351-60; (K) Blickling S., et al., *J Mol Biol*. (1997 Dec. 12); 274(4):608-21; (L) Kefala G., & Weiss M. S., *Acta Crystallogr Sect F Struct Biol Cryst Commun*. (2006 Nov. 1); 62(Pt 11):1116-9. Epub 2006 Oct. 20; and (M) Girish T. S., et al., *FEBS Lett*. (2008 Aug. 20); 582(19):2923-30. Epub 2008 Jul. 29. In embodiments the methods for identifying or designing a candidate inhibitor described herein can use the structural coordinates and/or biochemical activity from any one or any combination of one or more of a characterized DapA protein(s).

The term "N-Succinyl-L,L-DAP Desuccinylase," "Sapep," or "DapE" as used herein means an enzyme involved in the biosynthesis of lysine that (under appropriate conditions) catalyzes the reaction generates succinate and L,L-diaminopimelic acid from the substrate molecule N-succinyl-L,L-diaminopimelic acid. The term can include various DapE homologues, orthologs, variants, and fragments that can catalyze the biochemical reaction described above. Non-limiting examples of DapE are described herein for purposes of illustrative embodiments (for example, *Staphylococcus aureus* DapE as disclosed in SEQ ID NO: 2, FIG. 13(B)). Several dihydrodipicolinate synthases ("homologues") have been biochemically and structurally characterized such as, for example, those described in the following references (each of which is incorporated by reference herein): (A) Biagini, A. and Puigserver, A., *Comp Biochem Physiol B Biochem Mol Biol*, (2001) 128:469-481; (B) Chevrier, B., et al., *Eur J Biochem*, (1996) 273:393-398; (C) Greenblatt, H. M., et al., *J Mol Biol*, (1997) 265:620-636; (D) Linder, H. A., et al., *J Biol Chem*, (2003) 278:44496-44504; (E) Lundgren, S., et al., *J Biol Chem*, (2007) 282:36037-36047; (F) Munih, P., et al., *J Inorg Biochem*, (2007) 101:1099-1107; (G) Jozic, D., et al., *Structure* (2002) 10:1097-1106; (H) Rowsell, S., et al., *Structure*, (1997) 5:337-347.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

In a general sense, the disclosure relates to methods for identifying and/or designing active agents wherein the methods include identifying one or more proteins from an essential, biochemical pathway in a microbe. In various embodiments the method includes identifying and/or designing active agents that can act as inhibitors of microbial biological activity. In embodiments the therapeutic agents can bind to structural motifs in a protein wherein the structural motifs are not part of the active site of the protein. In some embodiments the therapeutic agents act as broad spectrum inhibitors of microbial biological activity, wherein the therapeutic agent inhibits one or more proteins from a single, essential biochemical pathway that is common to a plurality of microbes. In embodiments, the therapeutic agents inhibit one or more enzymes involved in the lysine biosynthetic pathway. In some embodiments the therapeutic agents act as inhibitors of *S. aureus* biological activity.

In another general sense, the disclosure relates to methods for identifying infective microbes (e.g., methicillin-resistant *S. aureus* (MRSA)) that involve detecting the presence of N-Succinyl-L,L-DAP Desuccinylase (DapE) by contacting a bacteria cell with a conjugate molecule that includes a compound that binds to N-succinyl-L,L-DAP desuccinylase (DapE) linked to a detectable signaling molecule.

Diagnosis of bacterial infection can be determined by routine methods. For example signs of S. aureus infection include unusually high concentrations of white blood cells and/or pus-filled sores as well as common signs of infection (e.g., fever, inflammation, soreness). Additional laboratory analysis can be made on fluid samples (blood, pus, or urine), X-rays (to locate internal abscesses and estimate the severity of infection), or needle biopsy (e.g., from bone tissue) with subsequent microscopic examination may be used to assess bone involvement. The infective agent can also be cultured in a laboratory (grown on or in nutrient medium) for eventual identification and characterization.

Accordingly, aspects relate to methods for identifying a bacterial cell that is resistant to methicillin (MRSA). In embodiments the bacterial cell is S. aureus. In various embodiments the method includes providing a bacterial cell; generating a conjugate molecule, wherein the conjugate molecule includes a compound that binds to N-Succinyl-L,L-DAP Desuccinylase (DapE) linked to a detectable signaling molecule; contacting the bacterial cell with the conjugate molecule under conditions that allow for binding of the conjugate molecule with DapE; and detecting the presence or absence of conjugate molecule associated with the bacterial cell, wherein the bacterial cell is identified as a methicillin-resistant strain of bacteria when an amount of conjugate molecule associated with the bacterial cell is detected.

In embodiments the bacteria is present in a biological sample. In embodiments the biological sample is derived from a mammal such as, for example, a human. In further embodiments the biological sample is a fluid such as the non-limiting examples of blood, serum, pleural fluid, cerebrospinal fluid, saliva, pus, or urine. In some embodiments the bacteria is cultured from a test swab sample, for example, a surface swab.

The conjugate molecule can be generated using common techniques and common linker moieties. In embodiments the conjugate molecule is generated such that the linker moiety and the signaling molecule do not interfere with or affect the DapE binding affinity of the compound that binds to DapE. In embodiments the detectable signaling molecule includes any moiety that can be detected such as, for example, a radiolabel, an enzyme, a fluorophore, a dye, or any other moiety that provides a detectable signal.

In some embodiments the conjugate molecule compound that binds to DapE includes a polynucleotide, a DapE inhibitor, a protein, or an antibody that has binding affinity to DapE. In embodiments the compound that binds to DapE includes a DapE small molecule inhibitor of DapE. In embodiments the compound that binds to DapE includes a small molecule inhibitor of DapE that is identified or designed by the methods described herein.

In some embodiments, the method can include mesoporous materials such as the non-limiting examples of metal oxides (e.g., $Al_2O_3$) and amine functionalized mesoporous silica (e.g., MCM-48) for sustained or delayed release of conjugates that incorporate one or more DapE inhibitor molecules. The release profile and characteristics of such systems can be adjusted by modification of the material pore size and shape, overall structure, and surface chemistry [See, Kapoor, et al., J. Phys. Chem. B., 114: 3117-3121; "Inhibition of a Protein Tyrosine Phosphatase Using Mesoporous Oxides". Accordingly, these mesoporous materials can be modified to suit particular chemical requirements that are based on the components of conjugate molecules, allowing for optimization of pore size or surface chemistry (e.g., charge, solubility, etc.) based on the detectable signaling molecule and the DapE binding molecule.

In embodiments the bacterial cell is identified as methicillin-resistant when an amount of conjugate molecule associated with the bacterial cell that is detected is at least 25% (e.g., about 30%, 40%, 50%, 60%, 70%, 80%, 90%, 95%, or about 100%) above background control level. In embodiments the bacterial cell is identified as methicillin-resistant when an amount of conjugate molecule associated with the bacterial cell that is detected is at least about 50% above background control. In embodiments the bacterial cell is identified as methicillin-resistant when an amount of conjugate molecule associated with the bacterial cell that is detected is at least about 60% above background control. In embodiments the bacterial cell is identified as methicillin-resistant when an amount of conjugate molecule associated with the bacterial cell that is detected is at least about 70% above background control. In embodiments the bacterial cell is identified as methicillin-resistant when an amount of conjugate molecule associated with the bacterial cell that is detected is at least about 80% above background control. In embodiments the bacterial cell is identified as methicillin-resistant when an amount of conjugate molecule associated with the bacterial cell that is detected is at least about 90% above background control. In embodiments the bacterial cell is identified as methicillin-resistant when an amount of conjugate molecule associated with the bacterial cell that is detected is at least about 100% above background control.

In embodiments, the assay provides improved detection relative to existing assays for MRSA detection (e.g., Penicillin Binding Protein 2a, "PBP2a") which suffer from a number of false positive results (e.g., because PBP2a is not specific to MRSA). In embodiments the conjugate molecules of the assay bind DapE with high affinity (e.g., at least about 10 µM) and selectivity. In embodiments the assay can incorporate the conjugate molecule attached to a solid support such as, for example, plate substrates (e.g., microchips, microplates, microliter plates, etc.); particles (e.g., nanoparticles, microparticles, beads, etc.), or incorporated in gels. The materials for such substrates are known to those of skill in the art and can include, for example, polymers (e.g., plastics), latex, metal (e.g., paramagnetic or diamagnetic metals and alloys), glass, ceramic, and the like.

Aspects provide methods for identifying or designing a candidate inhibitor that binds to a site of dihydrodipicolinate synthase (DapA) or a homologue or active fragment thereof, including: obtaining the structure coordinates of amino acids of DapA or a homologue or active fragment thereof; generating a three-dimensional model of DapA or a homologue or active fragment thereof using the structure coordinates of the amino acids from DapA, wherein the model includes a root mean square deviation from backbone atoms of said amino acids of not more than ±1.0 Å; determining a binding site of DapA or a homologue or active fragment thereof from the three-dimensional model; and performing a computer fitting analysis to identify the candidate inhibitor that interacts with the binding site.

In embodiments that include the design of a candidate inhibitor, the computer fitting analysis of the interaction between the candidate inhibitor and the binding site predicts that DapA activity will be inhibited. In embodiments, the candidate inhibitor will be predicted to interact with the DapA binding site at a range typical for bonding interaction (e.g., from about 1.5 Å to about 4.0 Å). In embodiments, the inhibitor comprises a Ki value of about 1 nM to about 100 µM. In embodiments, the inhibitor comprises an IC50 value of about 1 nM to about 100 µM.

In embodiments the candidate inhibitor binds to *S. aureus* DapA (SEQ ID NO:1) or active fragment thereof. In embodiments the *S. aureus* is a methicillin resistant strain of *S. aureus* (MRSA).

In embodiments the method can further include contacting the identified candidate inhibitor with DapA or homologue or active fragment thereof under conditions that allow for determination the effect of the inhibitor on *S. aureus* biological activity.

In embodiments the candidate inhibitor binds to a region of DapA or homologue or active fragment thereof, wherein the region includes the L-Lysine binding pocket. In embodiments the L-Lysine binding pocket includes Lys-86 of SEQ ID NO:1. In further embodiments the L-Lysine binding pocket includes Ser-50, Lys-56, Asn-82, Lys-86, and Tyr-108 of SEQ ID NO:1. In embodiments the candidate inhibitor binds to one amino acid residue at the DapA L-Lysine binding pocket. In embodiments the candidate inhibitor binds to two amino acid residues at the DapA L-Lysine binding pocket. In embodiments the candidate inhibitor binds to three amino acid residues at the DapA L-Lysine binding pocket. In embodiments the candidate inhibitor binds to four amino acid residues at the DapA L-Lysine binding pocket. In embodiments the candidate inhibitor binds to five amino acid residues at the DapA L-Lysine binding pocket.

In embodiments the candidate inhibitor binds to a region of the L-Lysine binding pocket of DapA or homologue or active fragment thereof, wherein the candidate inhibitor binds to the L-Lysine binding pocket through charge-based (ionic) interaction. In embodiments the candidate inhibitor binds to a region of the L-Lysine binding pocket of DapA or homologue or active fragment thereof, wherein the candidate inhibitor binds to the L-Lysine binding pocket through hydrogen-bonding interaction. In embodiments the candidate inhibitor binds to a region of the L-Lysine binding pocket of DapA or homologue or active fragment thereof, wherein the candidate inhibitor binds to the L-Lysine binding pocket through interaction based on hydrophobic or hydrophilic characteristics (non-ionic). In embodiments the candidate inhibitor binds to a region of the L-Lysine binding pocket of DapA or homologue or active fragment thereof, wherein the candidate inhibitor binds to the L-Lysine binding pocket through steric interaction.

In embodiments the candidate inhibitor binds to a region of the L-Lysine binding pocket of DapA or homologue or active fragment thereof, such that the candidate inhibitor is predicted to bind to the DapA L-Lysine binding pocket with an affinity equal to or greater than the affinity of L-Lysine to the binding pocket. In embodiments the candidate inhibitor is predicted to bind to the DapA L-Lysine binding pocket with an increased affinity of at least about 5% to about 100% or more than the affinity of L-Lysine to the binding pocket (e.g., about 5%, 10%, 15%, 20%, 25%, 30%, 35%, 40%, 45%, 50%, 55%, 60%, 65%, 70%, 75%, 80%, 85%, 90%, 95%, 100%, 105%, or about 110%).

In embodiments, the candidate inhibitor binds to at least 1 amino acid of the DapA binding site at a range typical for bonding interaction (e.g., from about 1.5 Å to about 4.0 Å). In embodiments, the inhibitor comprises a Ki value of about 1 nM to about 100 µM. In embodiments, the inhibitor comprises an IC50 value of about 1 nM to about 100 µM.

Aspects provide methods for identifying or designing a candidate inhibitor that binds to a site of N-Succinyl-L,L-DAP desuccinylase (DapE) or a homologue or active fragment thereof, including: obtaining the structure coordinates of amino acids of DapE or homologue or active fragment thereof; generating a three-dimensional model of DapE or homologue or active fragment thereof using the structure coordinates of the amino acids from the DapE, wherein the model includes a root mean square deviation from backbone atoms of said amino acids of not more than ±1.0 Å; determining a binding site of DapE or homologue thereof from the three-dimensional model; and performing a computer fitting analysis to identify the candidate inhibitor that interacts with the binding site.

In embodiments that include the design of a candidate inhibitor, the computer fitting analysis of the interaction between the candidate inhibitor and the binding site predicts that DapE activity will be inhibited by the restriction of movement of the lid domain.

In embodiments the candidate inhibitor binds to *S. aureus* DapE (SEQ ID NO:2) or active fragment thereof. In embodiments the *S. aureus* is a methicillin resistant strain of *S. aureus* (MRSA).

In embodiments the candidate inhibitor binds to a region of DapE or homologue or active fragment thereof, wherein the region includes the amino acid residues at the interface of the catalytic domain and the lid domain. (See, e.g., FIG. 2). In embodiments the amino acid residues at the interface of the catalytic domain and the lid domain include amino acid residues Glu-150, Asn-216, His-269, Arg-350, Thr-412, Gly-416, and His-440 of SEQ ID NO:2. In further embodiments the interface of the catalytic domain and the lid domain can include any one or more amino acid residues Glu-150, Ser-151, His-180, Gly-181, Glu-182, Lys-183, Arg-214, Asn-216, His-269, Arg-350, His-384, Tyr-385, Asp-387, Lys-388, Thr-412, Gly-416, or His-440 of SEQ ID NO:2. In embodiments the catalytic domain and the lid domain includes any one or more amino acid residues Glu-150, Ser-151, His-180, Gly-181, Glu-182, Lys-183, Arg-214, Asn-216, His-269, Arg-350, His-384, Tyr-385, Asp-387, Lys-388, Thr-412, Gly-416, or His-440 of SEQ ID NO:2.

In embodiments the candidate inhibitor binds to one amino acid residue at the DapE domain interface. In embodiments the candidate inhibitor binds to two amino acid residues at the DapE domain interface. In embodiments the candidate inhibitor binds to three amino acid residues at the DapE domain interface. In embodiments the candidate inhibitor binds to four amino acid residues at the DapE domain interface. In embodiments the candidate inhibitor binds to five amino acid residues at the DapE domain interface. In embodiments the candidate inhibitor binds to six amino acid residues at the DapE domain interface. In embodiments the candidate inhibitor binds to seven amino acid residues or more that are located at the DapE domain interface.

In embodiments, the computer fitting analysis of the interaction between the candidate inhibitor and the binding site predicts that DapE activity will be inhibited. In embodiments, the candidate inhibitor will be predicted to interact with the DapE binding site at a range typical for bonding interaction (e.g., from about 1.5 Å to about 4.0 Å). In embodiments, the inhibitor comprises a Ki value of about 1 nM to about 100 µM. In embodiments, the inhibitor comprises an IC50 value of about 1 nM to about 100 µM.

In embodiments the candidate inhibitor binds to *S. aureus* DapE (SEQ ID NO:2) or active fragment thereof. In embodiments the *S. aureus* is a methicillin resistant strain of *S. aureus* (MRSA).

In embodiments the method can further include contacting the identified candidate inhibitor with DapE or homologue or active fragment thereof under conditions that allow for determination the effect of the inhibitor on *S. aureus* biological activity.

In embodiments the candidate inhibitor binds to a region of the DapE domain interface or DapE homologue or active fragment thereof, wherein the candidate inhibitor binds to the domain interface through charge-based (ionic) interaction. In embodiments the candidate inhibitor binds to a region of the domain interface of DapE or homologue or active fragment thereof, wherein the candidate inhibitor binds to the domain interface through hydrogen-bonding interaction. In embodiments the candidate inhibitor binds to a region of the domain interface of DapE or homologue or active fragment thereof, wherein the candidate inhibitor binds to the domain interface through interaction based on hydrophobic or hydrophilic characteristics (non-ionic). In embodiments the candidate inhibitor binds to a region of the domain interface of DapE or homologue or active fragment thereof, wherein the candidate inhibitor binds to the domain interface through steric interaction.

In embodiments the candidate inhibitor binds to a region of the domain interface of DapE or homologue or active fragment thereof, such that the candidate inhibitor is predicted to bind to the DapE domain interface with an affinity equal to or greater than the affinity of DapE inhibitors such as, for example, thiol-based agents (e.g., captopril). In embodiments the candidate inhibitor is predicted to bind to the DapE with an increased affinity of at least about 5% to about 100% or more than the affinity of captopril (e.g., about 5%, 10%, 15%, 20%, 25%, 30%, 35%, 40%, 45%, 50%, 55%, 60%, 65%, 70%, 75%, 80%, 85%, 90%, 95%, 100%, 105%, or about 110% or more).

In embodiments, the candidate inhibitor binds to at least 1 amino acid of the DapE domain interface at a range typical for bonding interaction (e.g., from about 1.5 Å to about 4.0 Å). In embodiments, the inhibitor comprises a Ki value of about 1 nM to about 100 µM. In embodiments, the inhibitor comprises an IC50 value of about 1 nM to about 100 µM.

In embodiments, the activity of the candidate inhibitor can be determined using a peptidase or lactamase assay and measuring the inhibitor's effect relative to a control.

In embodiments the fitting analysis of the interaction between the candidate inhibitor and the binding site is reviewed and selected based on those fits that predict that the inhibitor will bind at the interface between the catalytic domain and the lid domain. In embodiments the fitting analysis of the interaction between the candidate inhibitor and the binding site is reviewed and selected based on those fits that predict that the inhibitor will bind at the interface between the catalytic domain and the lid domain and restrict inter-domain movement between the catalytic domain and lid domain. In embodiments the fitting analysis predicts that the inhibitor will bind at the interface between the catalytic domain and lid domain so as to prevent the movement of the lid domain into a "closed" position with respect to the catalytic domain.

In embodiments the method can further include contacting the identified candidate inhibitor with DapE Or homologue or active fragment thereof under conditions that allow for determination the effect of the inhibitor on *S. aureus* biological activity.

Aspects provide computer readable media having stored therein instructions executable by a computing device to cause the computing device to perform the functions of:

obtaining structure coordinates of amino acids of DapA or DapE; obtaining structure data for the one or more candidate inhibitors; fitting the structure data for the one or more candidate inhibitors to the structure coordinates of amino acids of DapA or DapE; generating a fit value for the one or more candidate inhibitors; comparing the fit value with a predetermined value; based on the comparison, determining whether the fit value for the one or more candidate inhibitors is within a predetermined value; classifying the fit value for the one or more candidate inhibitors as either a "good" fit if the fit value is within the predetermined value or a "bad" fit if the fit value is not within the predetermined value; and selecting the candidate inhibitors classified as a "good" fit for further evaluation of inhibitor activity against *S. aureus*; and discarding the candidate inhibitors classified as a "bad" fit.

Aspects provide systems configured to identify one or more candidate inhibitors of *Staphylococcus aureus* biological activity including: a computing device; a graphical user interface display; and a computer readable medium having stored therein instructions executable by the computing device to cause the computing device to perform the functions of: obtaining structure coordinates of amino acids of DapA or DapE or both; obtaining structure data for the one or more candidate inhibitors; fitting the structure data for the one or more candidate inhibitors to the structure coordinates of amino acids of DapA or DapE or both; generating a fit value for the one or more candidate inhibitors; comparing the fit value with a predetermined value; based on the comparison, determining whether the fit value for the one or more candidate inhibitors is within a predetermined value; classifying the fit value for the one or more candidate inhibitors as either a "good" fit if the fit value is within the predetermined value or a "bad" fit if the fit value is not within the predetermined value; and selecting the candidate inhibitors classified as a "good" fit for further evaluation of inhibitor activity against *S. aureus*; and discarding the candidate inhibitors classified as a "bad" fit.

Aspects provide compounds that inhibit the biological activity of *S. aureus* by interaction with N-Succinyl-L,L-DAP desuccinylase (DapE) or dihydrodipicolinate synthase (DapA), identified by a method that includes: obtaining the structure coordinates of amino acids of DapA or DapE, or homologue or active fragment thereof; generating a three-dimensional model of DapA or DapE, or homologue or active fragment thereof using the structure coordinates of the amino acids from the DapA or DapE, wherein the model includes a root mean square deviation from backbone atoms of said amino acids of not more than ±1.0 Å; determining a binding site of DapA or DapE, or homologue or active fragment thereof from the three-dimensional model; performing a computer fitting analysis to identify the candidate inhibitor that interacts with the binding site; and contacting the identified candidate inhibitor with DapA or DapE, or homologue or active fragment thereof under conditions that allow for determination the effect of the inhibitor on *S. aureus* biological activity.

Aspects provide pharmaceutical compositions including the compounds disclosed herein, in combination with a pharmaceutically acceptable formulation agent. In embodiments, the compounds can be provided as pharmaceutically acceptable salts such as, for example, basic or acidic addition salts. See, e.g., *Remington: The Science and Practice of Pharmacy,* 21$^{st}$ ed., Lippincott Williams & Wilkins, A Wolters Kluwer Company, Philadelphia, Pa. (2005).

Aspects provide methods for treating *S. aureus* infection in a subject that include administering to a subject in need of treatment at least one compound identified by the methods described herein. In some embodiments, the method treats or prevents an infection associated *S. aureus* selected from one or more of a skin or soft tissue infections, respiratory infections, pneumonia, sepsis, osteomyelitis, septic arthritis, endocarditis, and toxic shock syndrome.

Aspects provide medicaments that include a compound identified by the methods described herein, for use in the treatment of *S. aureus* infection or a condition associated with *S. aureus* infection. In embodiments, the *S. aureus* infection is associated with one or more of a skin or soft tissue infection, respiratory infection, pneumonia, sepsis, osteomyelitis, septic arthritis, endocarditis, and toxic shock syndrome.

Aspects provide methods of inhibiting *S. aureus* biological activity that include contacting a *S. aureus* cell with an amount of one or more compounds identified herein, wherein the amount is effective to inhibit *S. aureus* biological activity. In embodiments the method inhibits *S. aureus* biological activity in vitro. In embodiments the method inhibits *S. aureus* biological activity in vivo.

Lysine Biosynthetic Pathway

In *S. aureus*, as well as other microbes, a cluster of proteins are involved in cell-wall synthesis and lysine metabolism. The proteins involved in the synthesizing of diaminopimelic acid (the lysine biosynthetic pathway) are absent in mammals. Corresponding proteins (homologues, variants, and orthologs) are present in other species of bacteria which provides a common metabolic pathway across many members of the prokaryotic kingdom for targeted inhibition. In most plants and bacteria, lysine is synthesized from aspartate via the diaminopimelate pathway. In bacteria, this route also serves as a branch-point intermediate for cell-wall component synthesis. Accordingly proteins in the lysine biosynthetic pathway provide useful molecular targets for the design of anti-microbial compounds.

Embodiments provide for methods that allow the design of inhibitors that bind to specific structural motifs in a protein but do not interact with the active site. Some embodiments provide a multi-target approach for identifying and/or designing an antimicrobial compound, including analyzing structural data and biochemical activities of two *S. aureus* enzymes involved in lysine biosynthesis, dihydrodipicolinate synthase (DapA) and N-succinyl-L,L-DAP desuccinylase (DapE).

Biochemistry of Dihydrodipicolinate Synthase (DapA)

Dihydrodipicolinate synthase (DapA, also referred to as DHDPS) catalyzes the first committed step of Lysine biosynthesis, yielding two essential bacterial metabolites, meso-diaminopimelate (DAP) and L-lysine. The catalytic mechanism of DapA has been identified and follows ping-pong reaction kinetics. It catalyzes the condensation of pyruvate and aspartate semialdehyde (ASA) to form dihydrodipicolinate (DHDP). This reaction is initiated by the formation of a Schiff intermediate by the reaction of the epsilon N atom of Lysine 163 at the DapA active site with the C2 atom of the incoming pyruvate moiety. With the removal of a water molecule, this intermediate is further converted to an enamine intermediate that is then condensed with the second substrate, aspartate semialdehyde, to form an acyclic enzyme-bound intermediate.

The crystal structure of *S. aureus* DapA (SEQ ID NO: 1) has been solved at 2.2 Å resolution with pyruvate bound at the active site (Girish et al., 2008). From the structure, DapA is present as a dimer in the asymmetric unit of the crystal, and DapA has been found to be dimeric in solution. Homologues of DapA from other microbes such as, for example, *E. coli, T. maritima* and *M. tuberculosis* are all reported be multimeric. The active site is located at the interface between the monomers, toward the C-terminal end of a TIM barrel domain. The active site residues including Lys-163, Tyr-109, Tyr-135, and Thr-46 superimpose closely to the corresponding active site residues found in other DapA homologues. Without being limited by any particular mechanism, the active site residues are thought to facilitate proton transfer upon the binding of pyruvate at the active site. The design of a molecule that can prevent the activation of this enzyme can form a potential inhibitor. Several HTPA analogues with oxygen incorporated at position-4 have demonstrated inhibition of catalysis at millimolar concentrations (Coulter et al., 1999). However, the inventors are not aware of any known DapA inhibitor that exhibits inhibitory activity at lower concentrations (e.g., nanomolar).

DapA is the first rate-limiting enzyme of the Lysine biosynthesis pathway. It has been shown to be feed-back regulated by the end product, L-lysine. However, there is a gradation in the sensitivity of the enzyme to feedback inhibition: botanical DapA (*N. sylvestris*) is highly sensitive with an $IC_{50}$ of 15-20 µM, DapA from gram negative bacteria (*E. coli*) is less sensitive with an $IC_{50}$ of 100 mM, and DapA from gram positive bacteria (*S. aureus* and *M. tuberculosis*) are the least sensitive, having an $IC_{50}$ of 250 mM.

The DapA lysine binding site is well characterized based on data from the crystal structures derived from the *N. sylvestris* and *E. coli* homologues (each having been co-crystallized with L-lysine). Two molecules of L-Lysine bind at the monomer-monomer interface, with interactions between each of the Lysine molecules and the residues of both monomers. Major interactions that stabilize the bound Lysine include the interactions of α-carboxyl group of Lysine with a phenolic oxygen of Tyr-106, α-aminogroup with Asn-80 and Glu-84. Structural superimposition of the *E. coli* and *S. aureus* homologues of DapA suggests that the insensitivity to feed-back inhibition by L-Lysine for the *S. aureus* homologue may result from a substitution of Glu-84 in *E. coli* DapA by Lys-86 in the *S. aureus* enzyme. This substitution of a negatively charged residue by a positively charged residue substantially alters the charge at the binding site. The longer side chain of Lys-86 may sterically hinder the binding of the L-Lysine. As described herein the difference between the L-Lysine binding pocket in *S. aureus* DapA compared to *E. coli* DapA has been identified as an alternate site for the design of novel lead compounds that specifically inhibit the *S. aureus* biological activity (FIG. 1).

Biochemistry of N-Succinyl-L,L-DAP Desuccinylase (DapE)

The DapE enzyme requires a divalent metal co-factor for its activity. Sequence conservation reveals that the first hundred amino acids of this protein are highly conserved across species, and are similar to several metal dependent enzymes that catalyze the hydrolysis of amide linkages (Addlagatta et al., 2006). A conserved set of glutamate, aspartate and histidine residues play a major role in metal ligation and enzyme activity. The reaction catalyzed by this enzyme appears to be initiated by the binding of a water molecule to the metal-ion center before interacting with N-succinyl-L,L-diaminopimelic acid. Attack by the hydroxyl at the active site then leads to the breakdown of the substrate to release the products succinate and L,L-diaminopimelic acid. There are two distinct conformations of the lid domain vis-á-vis the catalytic domain which implies that a large inter-domain movement is necessary prior to catalysis. FIG. 2 depicts the difference between the Lid domain in a closed conformation (pepV in FIG. 2(A)) and an open conformation (DapE in FIG. 2(B)). As described herein this conformational feature provides another alternate site on DapE that effective for the design of non-competitive inhibitors. Accordingly, in embodiments the methods include use of a competitive inhibitor, such as a non-hydrolyzable dipeptide, in conjunction with a compound that inhibits activity by restricting the motion of the lid domain. Embodiments provide a structural template for the design of inhibitor compounds for this enzyme and its structural analogues. This approach is also likely to circumvent the complexities imposed by enzyme structural plasticity that has been demonstrated as a key contributor towards the emergence of broad-spectrum antibiotic resistance (Maurice et al., 2008).

In embodiments methods for identifying and/or designing antimicrobials utilize the crystal structures and biochemical data included herein. Thus the structural and biochemical characterization of DapA and DapE as provided herein forms the basis for the bioinformatic approach identified herein such as for example, the methods relating to the identification and design of inhibitor compounds. The bioinformatic approach described herein lends itself to the use of steric changes in protein structure, such as quaternary structure in the case of DapA, or inter-domain movements in the case of DapE for the design of inhibitors.

Figure 9:
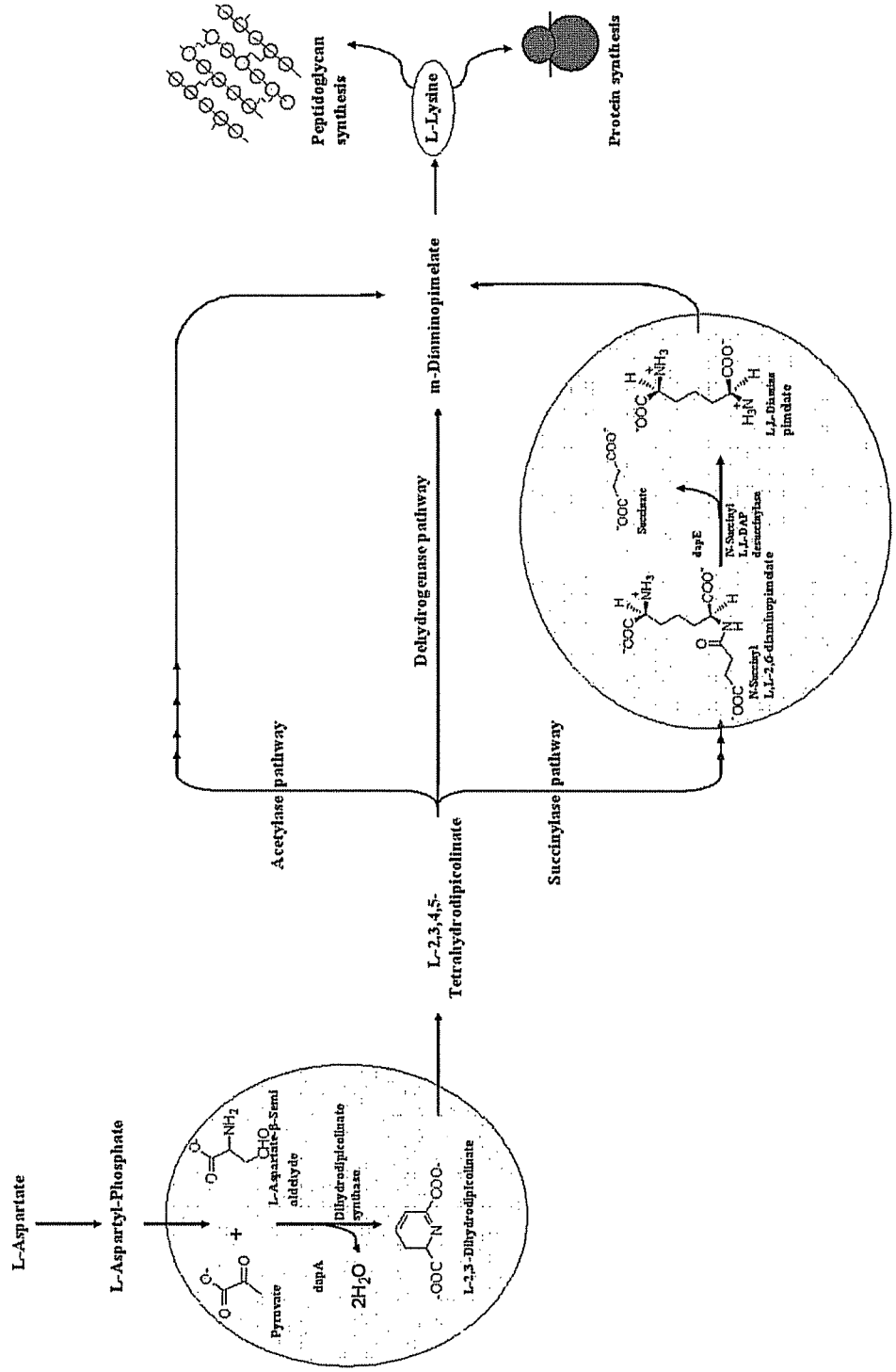
FIG. 9 depicts the general biochemical pathway for lysine biosynthesis of *S. aureus*.
Figure 10:
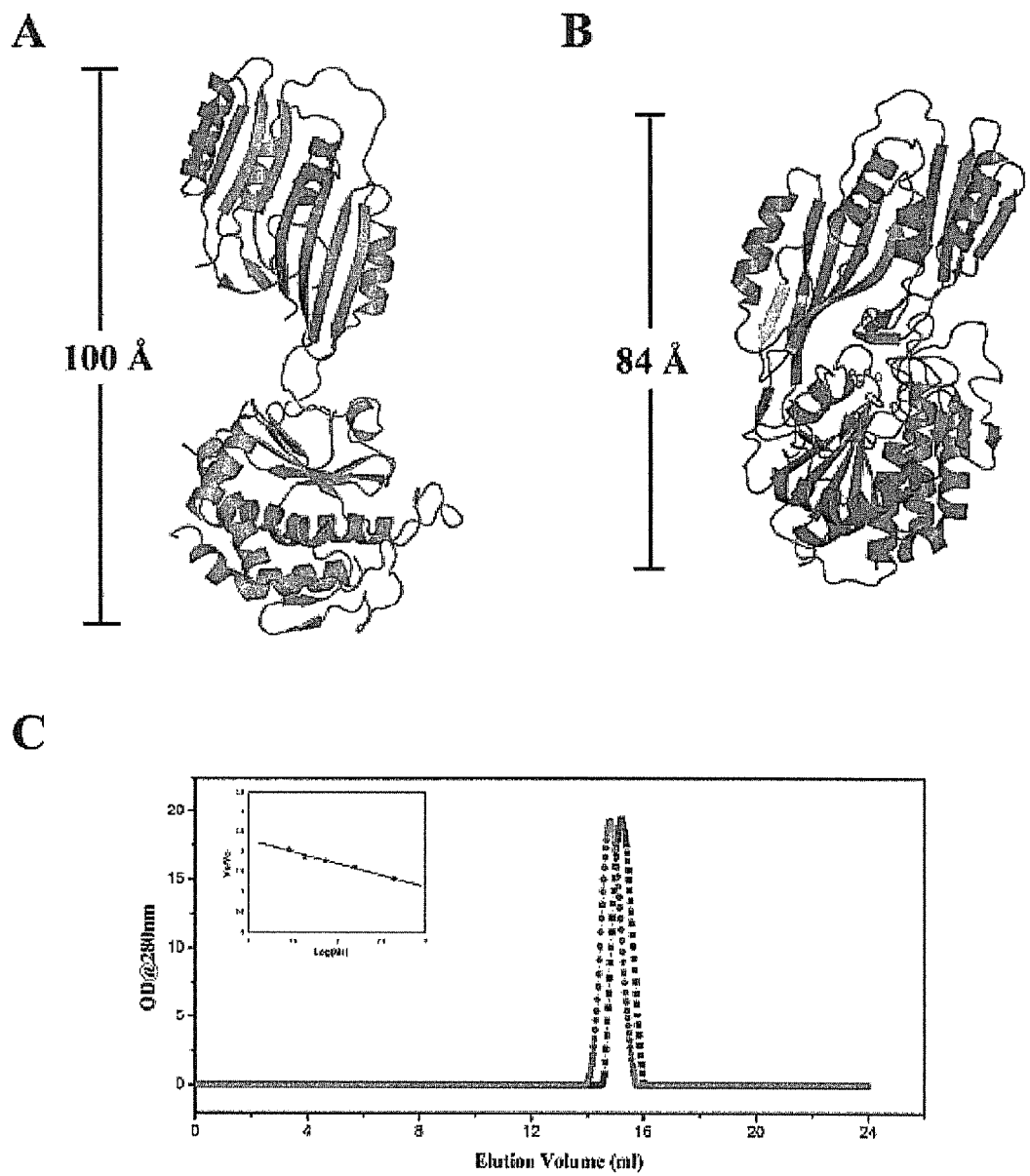
FIG. 10 depicts the general structure of the open (A) and closed (B) forms of DapE. (A) in the open form of the protein metal ions are not bound (apo-form); (B) in the closed form near the center, two $Mn^{2+}$ ions are bound at the active site and are shown as spheres and a bound phosphate group is depicted as a ball-and-stick model. The dimensions in both conformations were calculated using PDBSET. (C) Depicts the size-exclusion column chromatography profiles which suggest the shape of DapE in apo (circle) and holo (square) forms are different in solution (as well as in crystal form).
Figure 11:
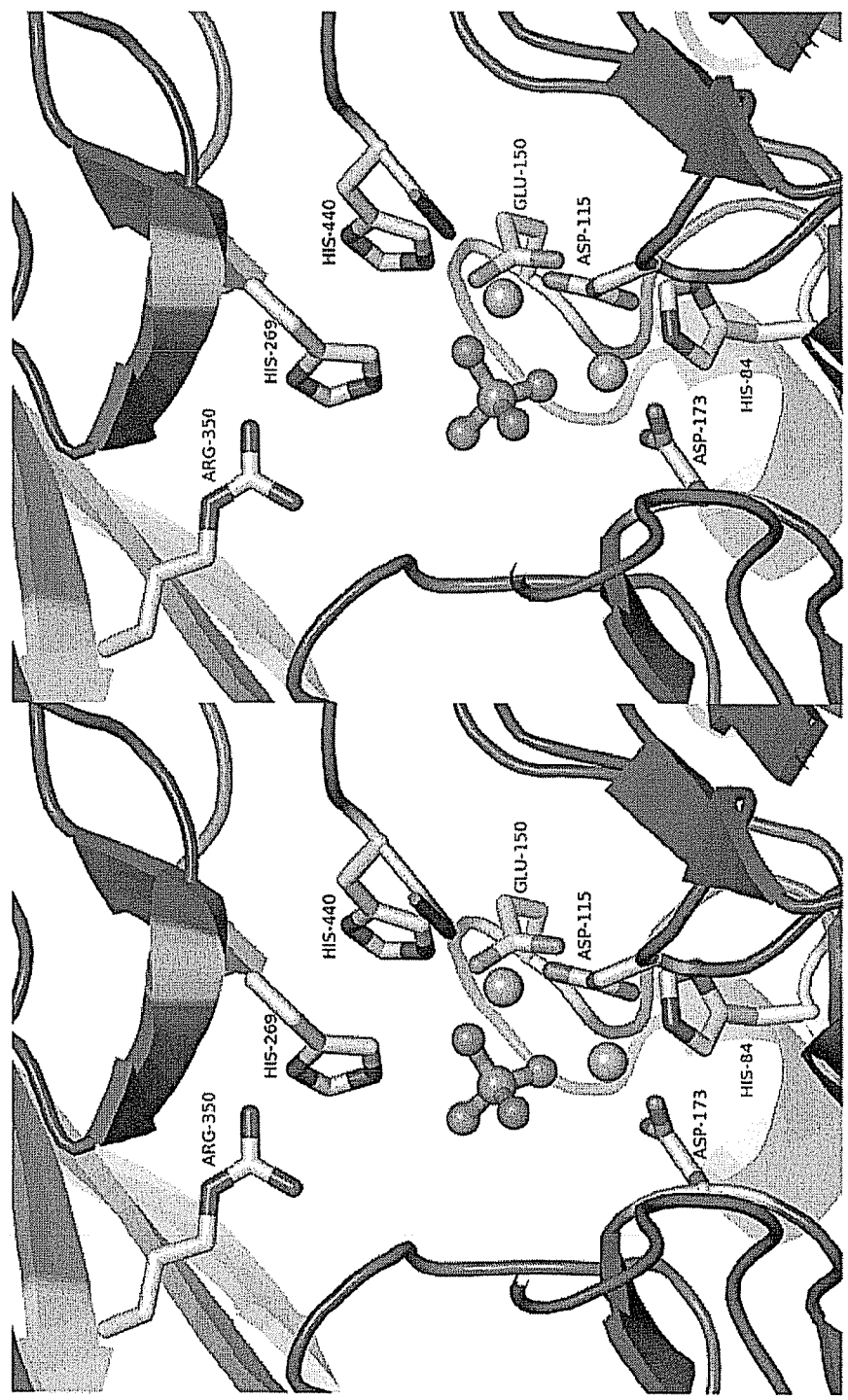
FIG. 11 depicts the active site of DapE. Stereo views of the active site in the closed form (A) and the open form (B) are provided. The residues that coordinate metal ion and that are involved in catalysis are shown in stick format (and labeled). (C) Depicts the super-position of the active site regions of DapE in the apo (medium gray) and $Mn^{2+}$ (dark gray) forms as well as the active site from PepV from *L. delbruki* (light gray).
Figure 11:
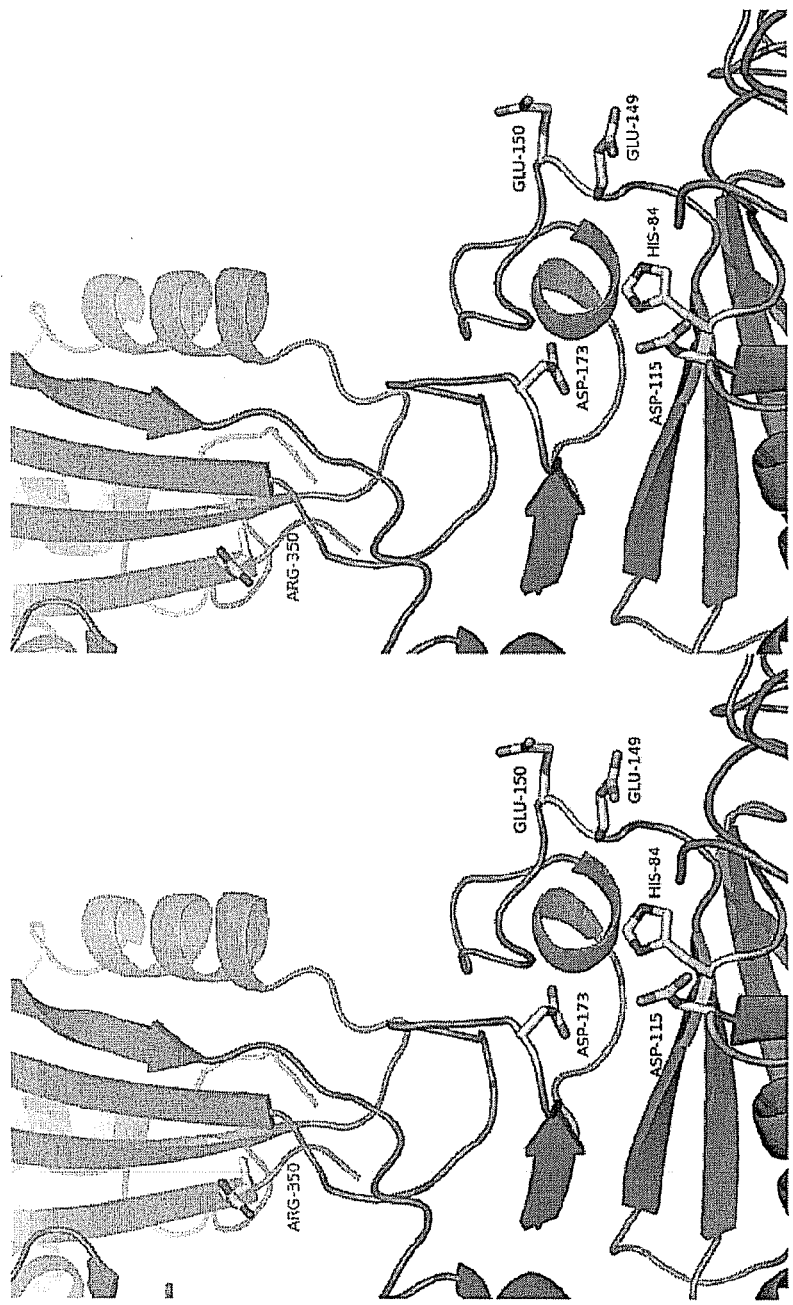
Figure 11:
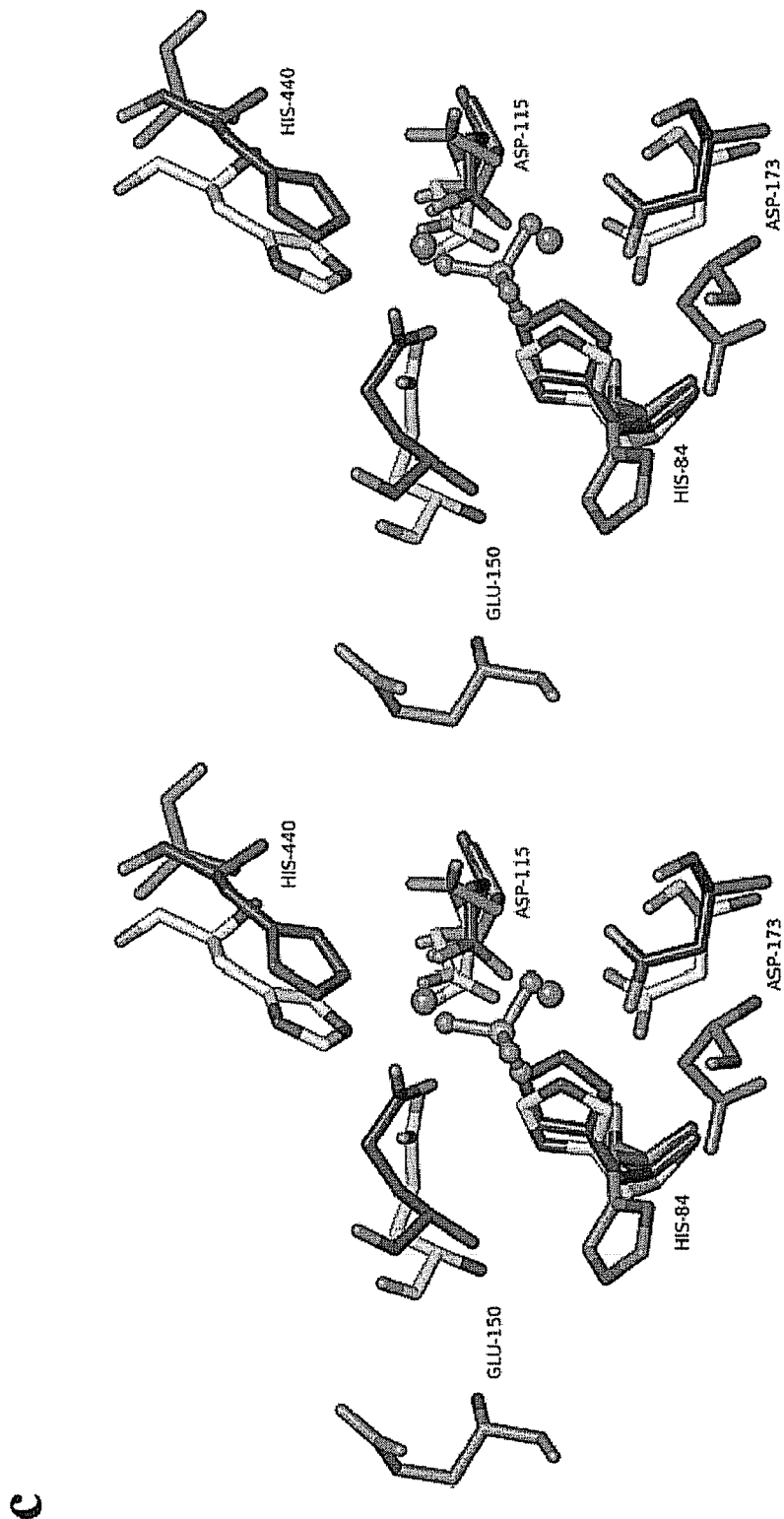
Figure 12:
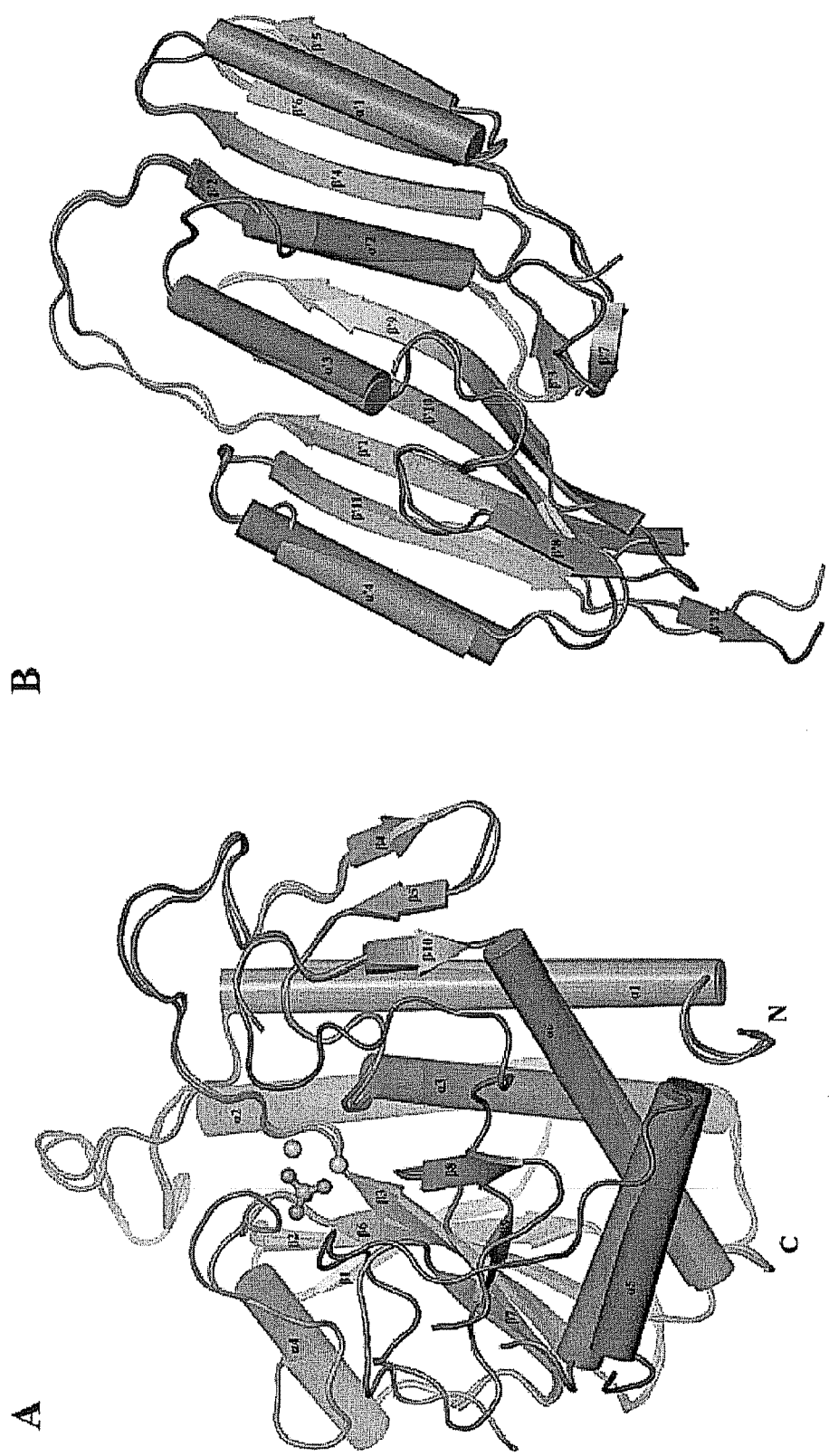
FIG. 12 depicts a regulatory mechanism of DapE. The catalytic (A) and lid (B) domain structures in the open and closed forms are super-imposed. Some differences in polypeptide chain conformations can be noted in each domain. (C) Super-positioning the open (medium gray) and closed (dark gray) form of the protein. A rotation of 71° was calculated between the open and closed conformations. The inset shows a 2mFo-DFc map electron density (at 1.0 σ level) at the location of the disulfide bond between Cys-155 and Cys-178 in the open form.
Figure 12:
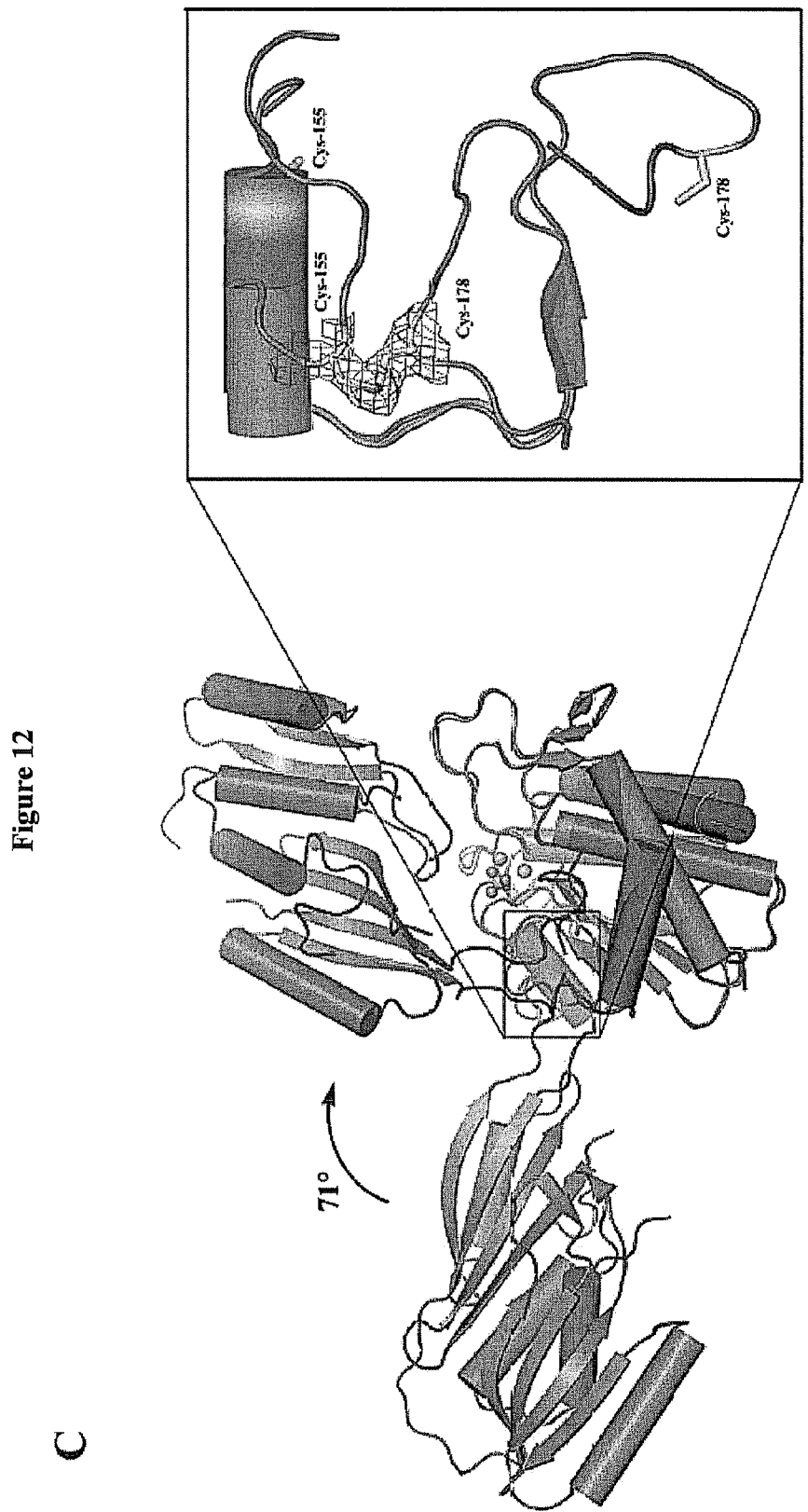

FIG. 9 depicts the lysine biosynthetic pathway in S. aureus. This pathway plays a dual role by providing Lysine for proteins synthesis as well as cell wall formation. The reactions catalyzed by the two enzymes DapA and DapE are highlighted in FIG. 9.

In embodiments, the methods described herein further include receiving a first input associated with a first possible dataset that includes receiving a first data entry from a graphical user interface.

In embodiments, the methods described herein further include receiving a first input associated with a first possible dataset that includes receiving a first data entry from at least one submission element of a graphical user interface.

In embodiments, the methods described herein further include receiving a first input associated with a first possible dataset that includes receiving a first data entry at least partially identifying one or more of one or more domains of a DapA structure, one or more shapes of a DapA structure, one or more charges of a DapA structure, or one or more functions of a DapA structure.

In embodiments, the methods described herein further include receiving a second input associated with a second possible dataset that includes receiving a first data entry associated with the second possible dataset, the first data entry including one or more of a parameters of one or more test compounds.

In embodiments, the methods described herein further include identifying one or more binding sites that include one or more groups of residue selected from glutamate, aspartate and histidine.

In embodiments, the methods described herein further include accessing the first input to acquire the data representative of the structure of N-Succinyl-L,L-DAP Desuccinylase (DapE).

In embodiments, the methods described herein further include generating a first possible dataset in response to the first input that includes generating the first possible dataset in response to the first input, the first input including one or more of a structure of DapA or DapE.

In embodiments, the methods described herein further include generating a first possible dataset in response to the first input that includes generating the first possible dataset from within a first database associated with a structure of DapA or DapE.

In embodiments, the methods described herein further include generating a second possible dataset in response to a second input that includes generating the second possible dataset from within the second database associated with one or more test compounds.

In embodiments, the methods described herein further include determining a graphical illustration of the first input and/or the second input.

In embodiments, the methods described herein further include determining a graphical illustration of the first input and the second input that includes determining the graphical illustration for inclusion in a display element of a graphical user interface.

In embodiments, the methods described herein further include determining a graphical illustration of the first input that includes performing an analysis of one or more elements of the first input to determine a first possible outcome; and determining the graphical illustration, based on the analysis.

In embodiments, the methods described herein further include determining a graphical illustration of the second input that includes performing an analysis of one or more elements of the second input to determine a first possible outcome; and determining the graphical illustration, based on the analysis.

In embodiments, the methods described herein further include determining a graphical illustration of the first input and/or the second input that includes performing an analysis of one or more elements of the first input, and/or the second input to determine a first possible outcome in each case, the first possible outcome including one or more of a possible risk, a possible risk, a possible result, or a possible consequence; and determining the graphical illustration in respect of each of the first input and the second input including one or more of a target or one or more target components in association with a visual indicator.

In embodiments, the methods described herein further include determining a graphical illustration of the first input and/or the second input that includes determining in each case a correlation between a first possible outcome and a type of a visual indicator used in the graphical illustration to represent the first possible outcome.

In embodiments, the methods described herein further include determining a graphical illustration of the first input and/or the second input that includes determining the graphical illustration of a first possible outcome for use of one or more of domains of a target structure, one or more shapes of a target structure, one or more changes of a target structures, one or more functions of a target structure.

In some embodiments, methods for identifying one or more compounds suitable for inhibiting microbial activity of S. aureus include utilizing computational analysis of structural motifs associated with activity of one or more enzymes from an essential biochemical pathway of S. aureus.

In some embodiments, methods for identifying one or more compounds suitable for inhibiting microbial activity of S. aureus include that involves designing S. aureus therapeutic agents based on the model of multiple-target inhibition.

In some embodiments, methods for identifying one or more compounds suitable for inhibiting microbial activity of S. aureus include utilizing computational analysis to design inhibitors configured to bind to specific structural motifs in a protein other than the active site.

As used herein the term "a system for" relates to hardware, software, and data storage media used to analyze atomic coordinate data. Typically the minimum hardware means of the computer-based systems includes one or more of, but is not limited to, a central processing unit (CPU), input means, output means and data storage means.

Embodiments provide a monitor to visualize structure data. The data storage means can be RAM or means for accessing computer readable media. Examples of such systems are microcomputer workstations available from Silicon Graphics Incorporated and Sun Microsystems running Unix based, Windows NT or IBM OS/2 operating systems.

By "fitting" is meant determining by automatic, or semi-automatic means, interactions between one or more atoms of an agent molecule and one or more atoms or binding sites of DapA or DapE, and calculating the extent to which such interactions are stable. Various computer-based methods for fitting are described further herein.

By "computer readable media" is meant any media which can be read and accessed directly by a computer e.g. so that the media is suitable for use in the above-mentioned computer system. Such media include, but are not limited to: magnetic storage media such as floppy discs, hard disc storage medium and magnetic tape; optical storage media such as optical discs or CD-ROM; electrical storage media such as RAM and ROM; and hybrids of these categories such as magnetic/optical storage media.

Figure 3:
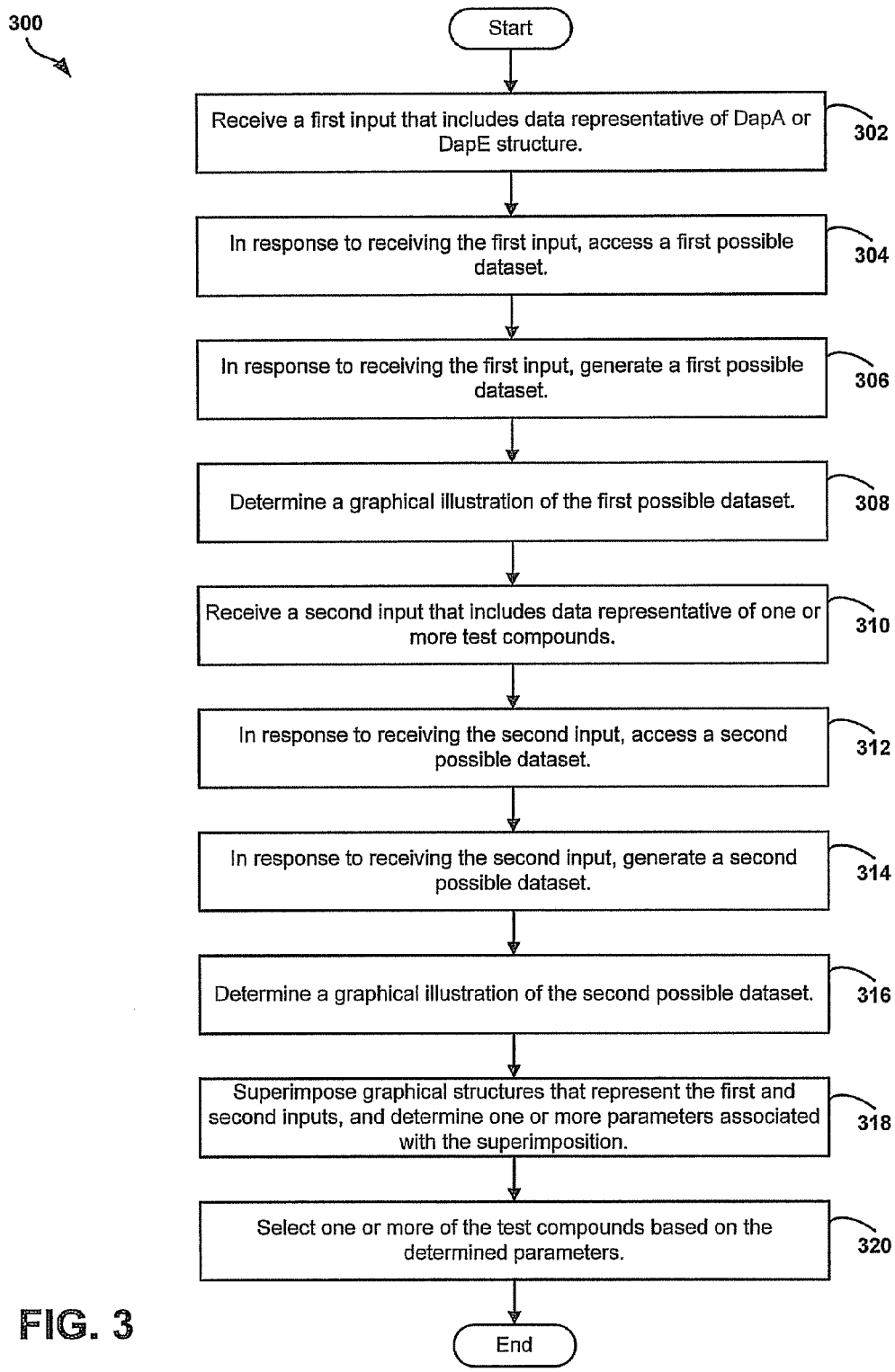
FIG. 3 shows an operational flow representing illustrative embodiments of operations related to determining one or more parameters for selecting one or more test compounds based on a first and second input.

After a start operation, as shown in FIG. 3, the operational flow (300) moves to a receiving operation (302) where a first input including data representative of the structure of dihydrodipicolinate synthase (DapA) or N-Succinyl-L,L-DAP Desuccinylase (DapE) is received. A first input may also include data representative of the identity and sequence of DapA or DapE.

An optional accessing operation (304) accesses a first possible dataset associated with the first input in response to receiving the first input. Data representative of the identity and sequence of DapA may also be accessed.

An optional generating operation (306) generates the first possible dataset in response to receiving the first input. For example, data representative of the identity and sequence of DapA may also be generated.

An optional determining operation (308) determines a graphical illustration of the first possible dataset. For example, data representative of the identity and sequence of DapA may also be graphically represented.

Then, the operational flow (300) moves to another receiving operation (310), where a second input including data representative of the structure of one or more test compounds is received.

An optional accessing operation (312) accesses a second possible data set associated with the second input in response to receiving the second input. An optional generating operation (314) generates the second possible dataset in response to receiving the second input. For example, data representative of the structure of one or more test compounds may also be generated. An optional determining operation (316) determines a graphical illustration of the second possible dataset.

A determining operation (318) superimposes the digitally-encoded representation of the graphical illustration relating to the first and second input, and determines one or more parameters associated with the output of the superimposition.

A selection operation (320), selects one or more of the test compounds based on the parameters determined at the operation (318).

Operations (302) to (320) may be performed with respect to a digital representation (e.g., digital data) of, for example, data representative of a structure of DapA, DapE, and/or one or more target compounds cause to target biological assembler components. The logic may accept a digital or analog (for conversion into digital) representation of an input and/or provide a digitally-encoded representative of a graphical illustration, where the input may be implemented and/or accessed locally or remotely.

Operations (302) to (320) may be performed related to either a local or a remote storage of the digital data, or to another type of transmission of the digital data. In addition to inputting, accessing, querying, recalling, calculation, determining or otherwise obtaining the digital data, operations may be performed related to storing, assigning, associating, displaying or otherwise archiving the digital data to a memory, including for example, sending and/or receiving a transmission of the digital data from a remote memory. Accordingly, any such operations may involve elements including at least an operator (e.g., human or computer) directing the operation, a transmitting computer, and/or receiving computer, and should be understood to occur in the United States as long as at least one of these elements resides in the United States.

Figure 4:
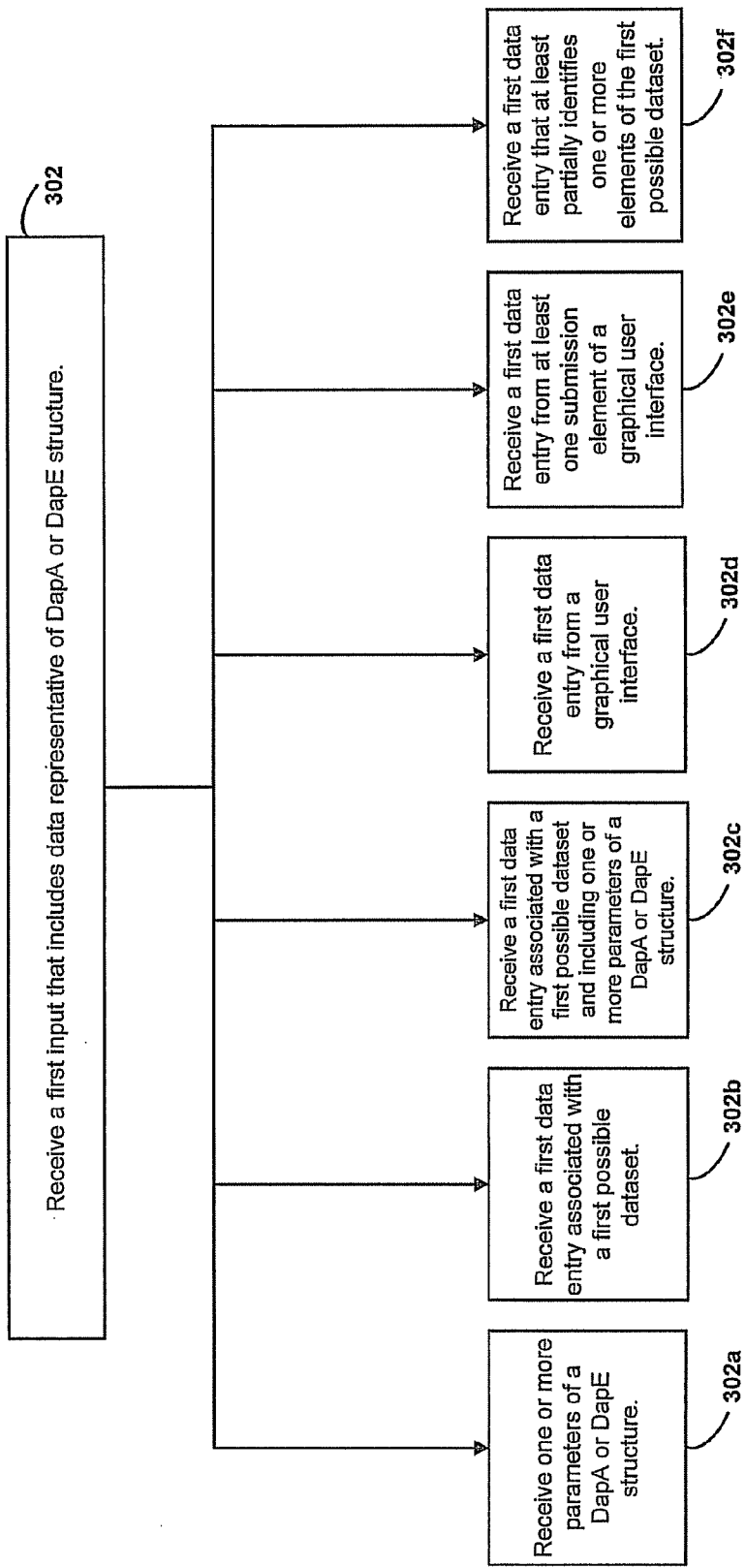
FIG. 4 shows optional embodiments of the operational flow of FIG. 3.

FIG. 4 shows illustrative embodiments of the receiving operation (302), receiving a first input including data representative of the structure of DapA or DapE, including operations receiving types of inputs and data entry and may include at least one additional operation. Receiving operations can optionally include, but are not limited to, operation (302a), operation (302b), operation (302c), operation (302d), operation (302e), and/or operation (302f).

At the optional operation (302a), the first input can include one or more of a parameter of the DapA or DapE structure. At the optional operation (302b), a first data entry associated with a first possible dataset may be received. At the optional operation (302f), a first data entry at least partially identifying one or more elements of the first possible dataset may be received.

At the optional operation (302c), a first data entry associated with a first possible dataset may be received that may include one or more parameter of the DapA or DapE structure.

At the optional operation (302d), a first data entry may be received from a graphical user interface, or at the optional operation (302e), from at least one submission element of a graphical user interface.

Figure 5:
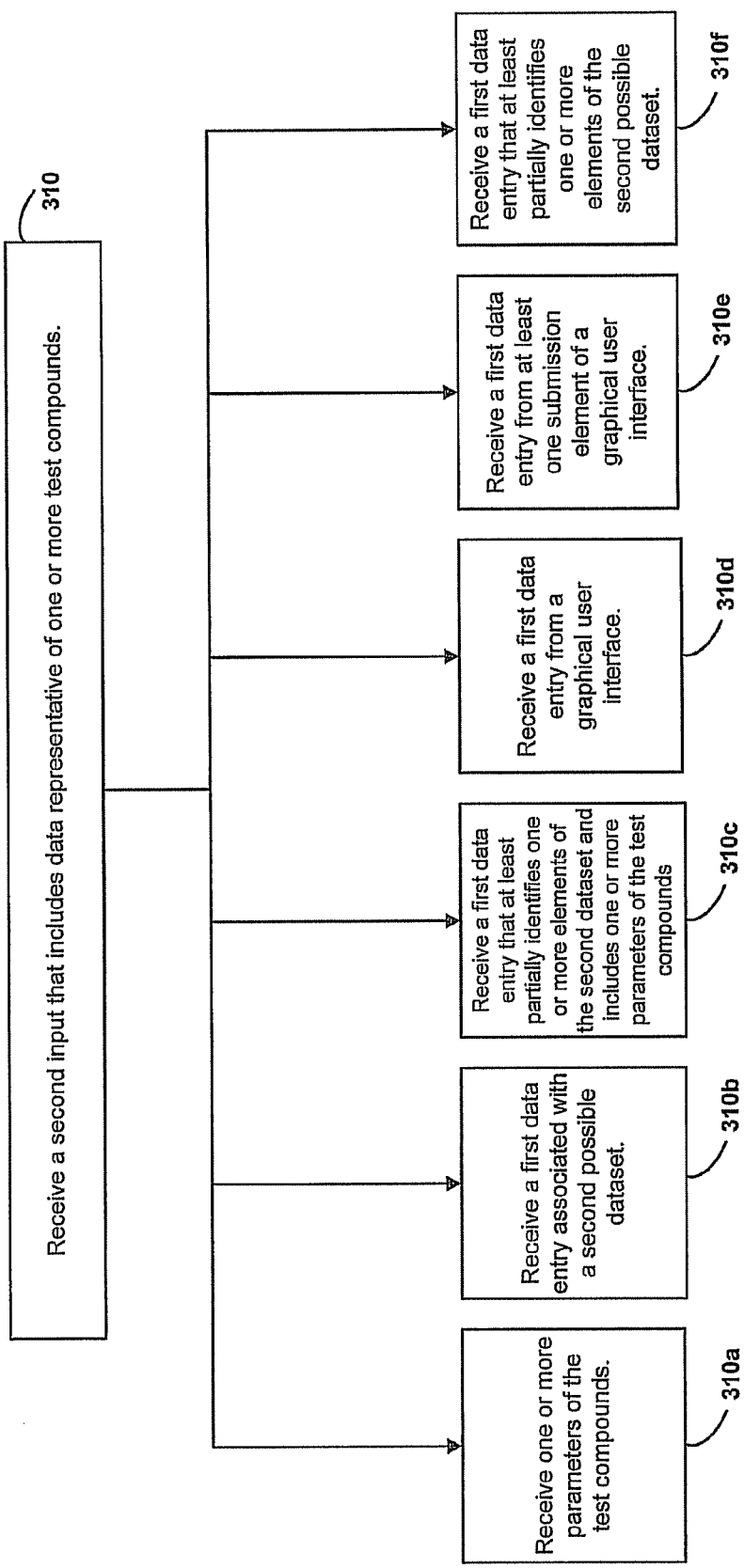
FIG. 5 shows optional embodiments of the operational flow of FIG. 4.

FIG. 5 shows illustrative embodiments of the receiving operation (310), receiving a second input including data representative of the structure of one or more test compounds, including operations receiving types of inputs and data entry and may include at least one additional operation. Receiving operations can optionally include operation (310a), operation (310b), operation (310c), operation (310d), operation (310e), and/or operation (310f).

At the optional operation (310a), the first input may include one or more parameters of the test compounds. At the operation (310b), a first data entry associated with a second possible dataset may be received. At the optional operation (302f), a first data entry at least partially identifying one or more elements of the second possible dataset may be received, and at the optional operation (310c), a first data entry at least partially identifying one or more elements of the second possible dataset may be received which may include one or more parameters of the test compounds.

At the optional operation (310d), a first data entry may be received from a graphical user interface, or at the optional operation (310e), from the at least one submission element of a graphical interface.

Figure 6:
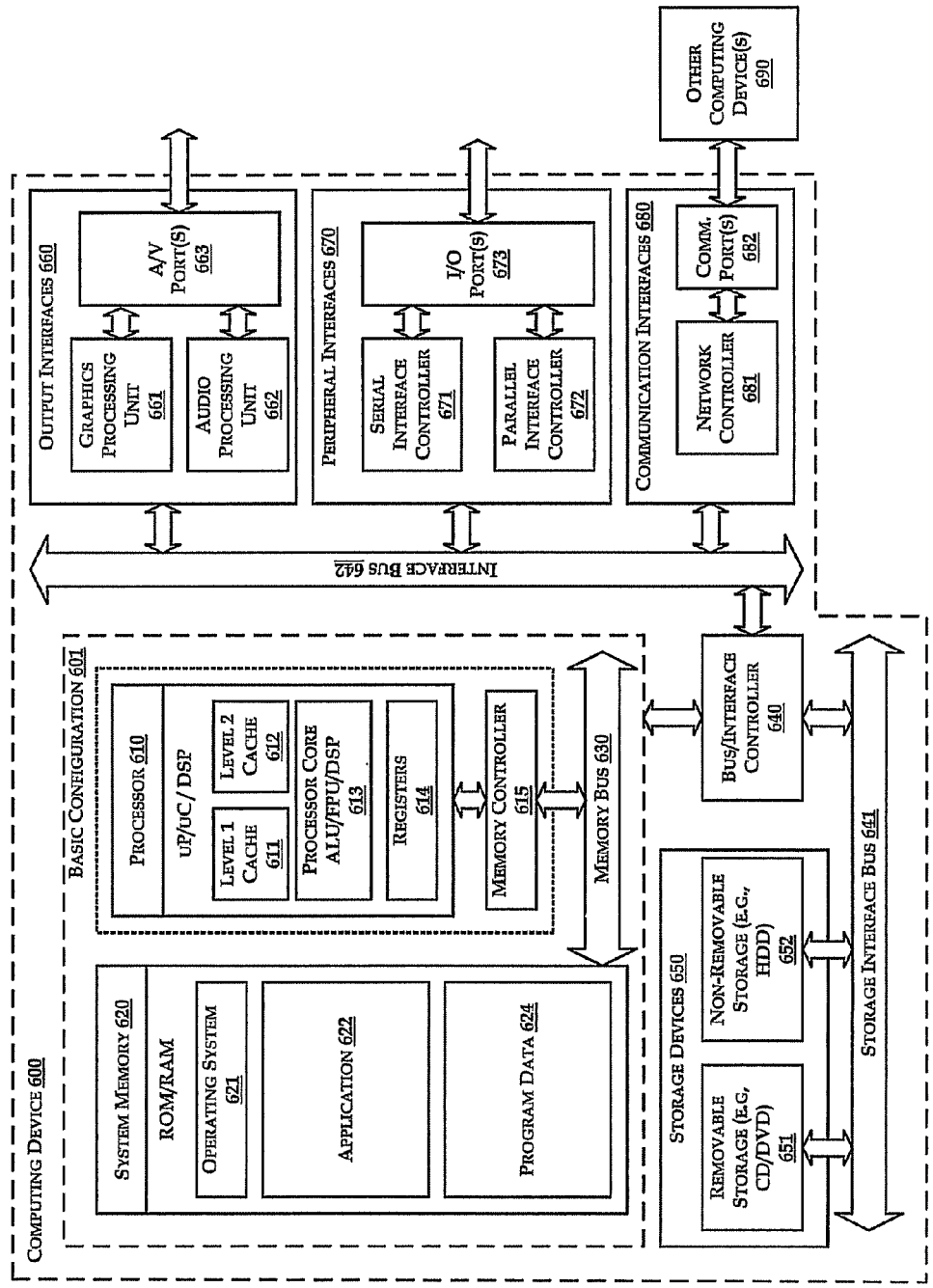
FIG. 6 is a block diagram of an illustrative embodiment of a computing device arranged for carrying out one or more methods described herein.

FIG. 6 is a block diagram depicting an example computing device (600) that may be configured to carry out one or more embodiments of the various aspects described herein.

In a very basic configuration (601), computing device (600) typically includes one or more processors (610) and system memory (620). A memory bus (630) can be used for communicating between the processor (610) and the system memory (620).

Depending on the desired configuration, processor (610) can be of any type including but not limited to a microprocessor (µP), a microcontroller (µC), a digital signal processor (DSP), or any combination thereof. Processor (610) can include one or more levels of caching, such as a level one cache (611) and a level two cache (612), a processor core (613), and registers (614). The processor core (613) can include an arithmetic logic unit (ALU), a floating point unit (FPU), a digital signal processing core (DSP Core), or any combination thereof. A memory controller (615) can also be used with the processor (610), or in some implementations the memory controller (615) can be an internal part of the processor (610).

Depending on the desired configuration, the system memory (620) can be of any type including but not limited to volatile memory (such as RAM), non-volatile memory (such as ROM, flash memory, etc.) or any combination thereof. System memory (620) typically includes an operating system (621), one or more applications (622), and program data (624).

Figure 7:
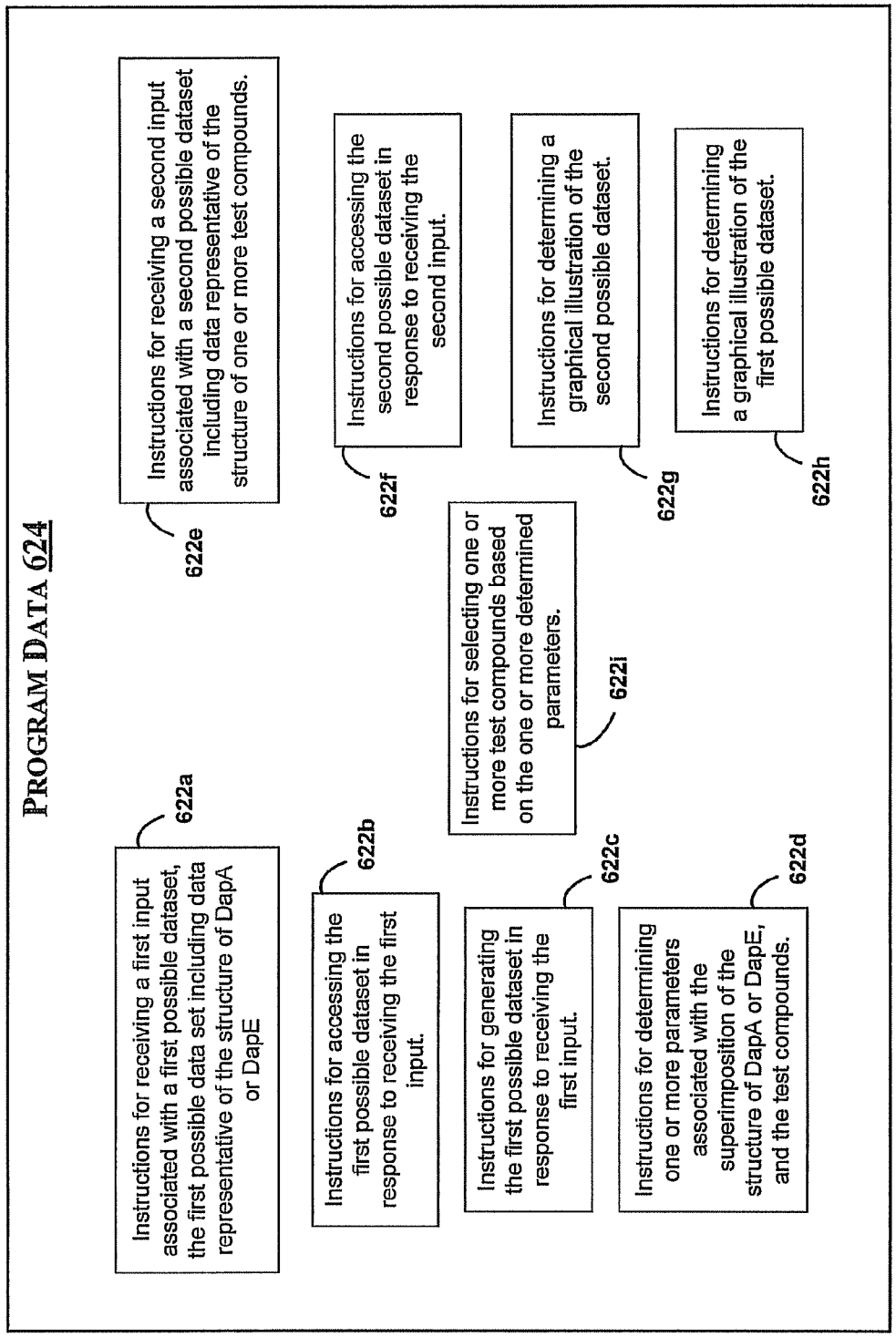
FIG. 7 shows a partial view of an illustrative embodiment of computer program instructions for executing a computer process on a computing device.
Figure 8:
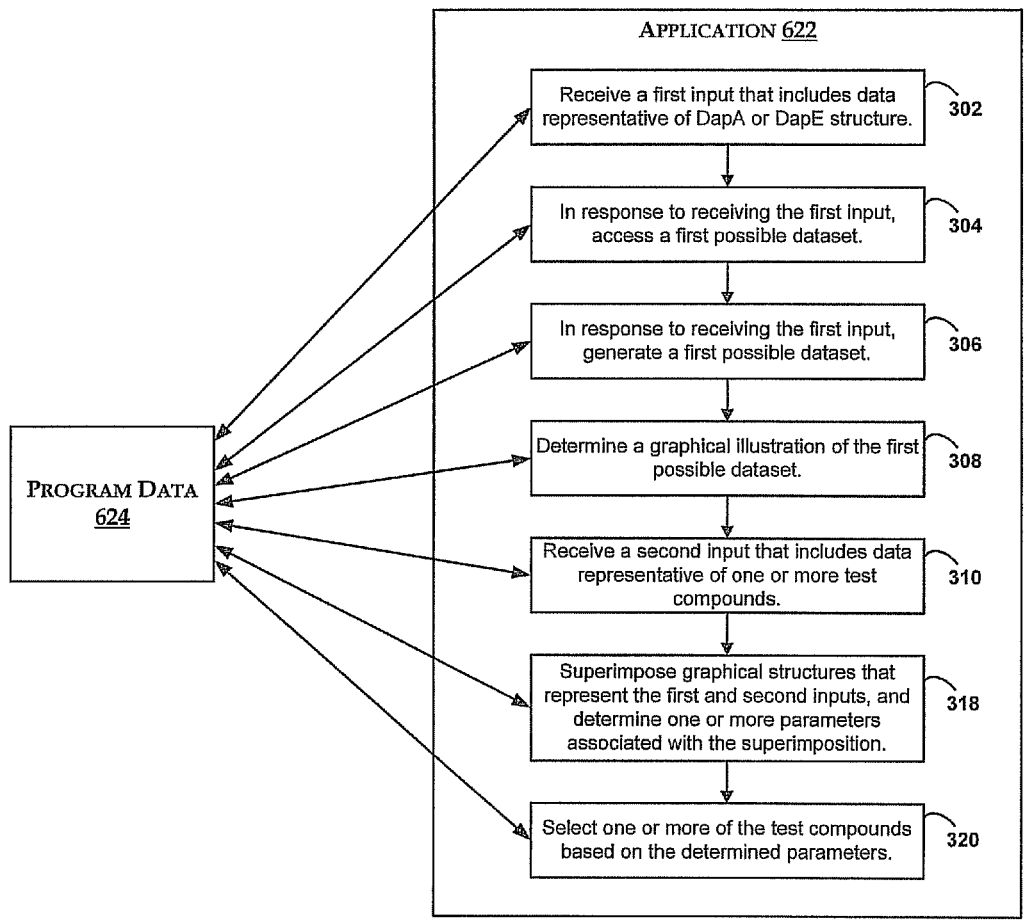
FIG. 8 shows an illustrative embodiment of carrying out select portions of the operational flow of FIG. 3 on portions of the computing device of FIG. 6.

Program data (624) may store operating instructions, which when executed by application (622) (or any other part of computing device 600) causes computing device 600 to carry out one or more of the steps of flow (300). For example, FIG. 7 shows a partial view of an illustrative computer program data (624) that includes operating instructions for executing a computer process on a computing device. Program data (624) may include: instructions 622a for receiving a first input, the first input including data representative of the structure of DapA or DapE; instructions (622b) for accessing a first possible dataset in response to the first input; instructions (622c) for generating the first possible dataset in response to the first input; instructions (622h) for determining a graphical illustration of the first possible dataset; instructions (622e) for receiving a second input, the second input including data representative of one or more test compounds; instructions (622f) for accessing the second possible data set in response to receiving the second input, instructions (622g) for determining a graphical illustration of the second possible dataset; instructions (622i) for selecting one or more test compounds based on the one or more determining parameters; and instructions (622d) for determining one or more parameters associated with the superimposition of the structure of DapA or DapE and the one or more test compounds. The foregoing instructions can be, for example, computer executable and/or logic implemented instructions.

Application (622) may carry out all or part of the disclosed algorithms. For example, of program data (624). The instructions of program data (624), when executed by the computing device (600) cause the application (622) to and computing device (600) to carry out one or more of the steps of flow (300). For example, executing one or more of the instructions stored in program data (624) may cause the computing device at step (302), to receive the first input, the first input including data representative of the structure of DapA or DapE; at step (304), optionally access a first possible dataset in response to the first input; at step (306), optionally generate the first possible dataset in response to the first input; at step (308), optionally determine a graphical illustration of the first possible dataset; at step (310), receive a second input, the second input including data representative of the structure of one or more test compounds; at step (318) superimpose the structure of one or more test compounds to the structure of the DapA or DapE and determine one or more parameters associated with the superimposition of the structure of DapA or DapE with the one or more test compounds; and at step (320), selecting one or more of one or more test compounds at least partially based on the one or more determined parameters.

In embodiments, the methods include receiving a first input, the first input including data representative of the structure of DapA or DapE; receiving a second input, the second input including data representative of one or more test compounds; superimposing the structure of the one or more test compounds with structure of DapA or DapE; determining one or more parameters associated with the superimposition, and selecting one or more test compounds at least partially based on one or more determined parameters.

In embodiments these methods may be used as part of one or more methods of identifying a compound for inhibiting microbial activity such as, for example, *S. aureus* activity, and/or identifying one or more compounds for inhibiting microbial activity of *S. aureus* and/or implemented on one or more apparatus (308) (FIG. 3), for target peptide synthesis.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the vehicle will vary with the context in which the processes and/or systems and/or other technologies are deployed. For example, if an implementer determines that speed and accuracy are paramount, the implementer may opt for a mainly hardware and/or firmware vehicles; if flexibility is paramount, the implementer may opt for a mainly software implementation; or, yet again alternatively, the implementer may opt for some combination of hardware, software, and/or firmware.

Computing device (600) can have additional features or functionality, and additional interfaces to facilitate communications between the basic configuration (601) and any required devices and interfaces. For example, a bus/interface controller (640) can be used to facilitate communications between the basic configuration (601) and one or more data storage devices (650) via a storage interface bus (641). The data storage devices (650) can be removable storage devices (651), non-removable storage devices (652), or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media can include volatile and nonvolatile, removable and non-removable media implemented in any method or technology for storage or information, such as computer readable instructions, data structures, program modules, or other data;

System memory (620), removable storage (651) and non-removable storage (652) are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device (600). Any such computer storage media can be part of device (600).

Computing device (600) can also include an interface bus (642) for facilitating communication from various interface devices (e.g., output interfaces, peripheral interfaces, and communication interfaces) to the basic configuration (601) via the bus/interface controller (640). Example output interfaces (660) include a graphics processing unit (661) and an audio processing unit (662), which can be configured to communicate to various external devices such as a display or speakers via one or more A/V ports (663). Example peripheral interfaces (660) include a serial interface controller (671) or a parallel interface controller (672), which can be configured to communicate with external devices such as input devices (e.g., keyboard, mouse, pen, voice input device, touch input device, etc.) or other peripheral devices (e.g., keyboard, mouse, pen, voice input device, touch input device, etc.) or other peripheral devices (e.g., printer, scanner, etc.) via one or more I/O ports (673). An example communication interface (680) includes a network controller (681), which can be arranged to facilitate communications with one or more communication ports (682). The Communication connection is one example of a communication media. Communication media may typically be embodied by computer readable instructions, data structures, program modules, or other data in a modulated data signal, such as a carrier wave or other transport mechanism, an includes any information delivery media. A "modulated data signal" can be a signal that has one or more of its characteristics set or changed in such a manner as to encode information in the signal. By way of example, and not limitation, communication media can include wired media such as a wired network or directed-wired connection, and wireless media such as acoustic, radio frequency (RF), infrared (IR) and other wireless media. The term computer readable media (or medium) as used herein can include both storage media and communication media.

Computing device (600) can be implemented as a portion of a microfluidic biochip. Computing device (600) can also be implemented as a personal computer including both laptop computer and non-laptop computer configurations.

Compounds, Compositions, and Methods of Treatment

Other aspects provide compounds that inhibit the biological activity of *S. aureus*, which have been identified by the methods described herein. Further aspects provide pharmaceutical compositions including such compounds, methods of treating *S. aureus* infection a subject using such compounds, medicaments including such compounds for use in the treatment of *S. aureus* infection, and methods of inhibiting *S. aureus* biological activity including such compounds.

A compound inhibits the biological activity of *S. aureus* when the $EC_{50}$ value for the compound is determined to inhibit *S. aureus* by at least 25% (e.g., 25%, 30%, 35%, 40%, 45%, 50%, 55%, 60%, 65%, 70%, 75%, 80%, 85%, 90%, 95%, or 100%, or more) relative to a control compound. In embodiments the inhibition of *S. aureus* is determined by any known biological, chemical, and/or biochemical assay that can evaluate microbial activity (e.g., culture growth, enzymatic activity, infective activity, etc.). Non-limiting examples of methods for determining activity are illustrated in the Examples below.

Aspects provide compositions including the above-described compounds, in combination with a pharmaceutically acceptable salt, vehicle, carrier, diluent, and/or adjuvant.

Compositions are provided that contain therapeutically effective amounts. The compounds may be formulated into suitable pharmaceutical preparations such as tablets, capsules, or elixirs for oral administration or in sterile solutions or suspensions for parenteral administration. Typically the compounds described above are formulated into pharmaceutical compositions using techniques and procedures commonly used by one skilled in the art.

About 1 to 500 mg of a compound or mixture of compounds or a physiologically acceptable salt or ester can be compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained. The compositions can be formulated in a unit dosage form, each dosage containing from about 2 to about 100 mg, or about 10 to about 30 mg of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient.

To prepare compositions, one or more compounds are mixed with a suitable pharmaceutically acceptable carrier. Upon mixing or addition of the compound(s), the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. The effective concentration is sufficient for lessening or ameliorating at least one symptom of the disease, disorder, or condition treated and may be empirically determined.

Pharmaceutical carriers or vehicles suitable for administration of the compounds provided herein include any such carriers known to those skilled in the art to be suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

Methods for solubilizing can be used when the compounds exhibit insufficient solubility for effective formulation. Such methods are known and include, but are not limited to, using cosolvents such as dimethylsulfoxide (DMSO), using surfactants such as Tween®, and dissolution in aqueous sodium bicarbonate. Derivatives of the compounds, such as salts or prodrugs may also be used in formulating effective pharmaceutical compositions.

The compounds can be administered orally, parenterally, (IV, IM, depo-IM, SQ, and depo SQ), sublingually, intranasally (inhalation), intrathecally, topically, or rectally. Dosage forms known to those of skill in the art are suitable for delivery of the compounds.

The concentration of the compound is effective for delivery of an amount upon administration that lessens or ameliorates at least one symptom of the disorder for which the compound is administered. In embodiments, the compositions are formulated for single dosage administration.

The compounds may be prepared with carriers that protect them against rapid elimination from the body, such as time-release formulations or coatings. Such carriers include controlled release formulations, such as, but not limited to, microencapsulated delivery systems. The active compound is included in the pharmaceutically acceptable carrier in an amount sufficient to exert a therapeutically useful effect in the absence of undesirable side effects on the subject treated. The therapeutically effective concentration may be determined empirically by testing the compounds in known in vitro and in vivo model systems for the treated disorder.

The compounds and compositions can be enclosed in multiple or single dose containers. The enclosed compounds and compositions can be provided in kits, for example, including component parts that can be assembled for use. For example, a compound inhibitor in lyophilized form and a suitable diluent may be provided as separated components for combination prior to use. A kit may include a compound inhibitor and a second therapeutic agent for co-administration. The inhibitor and second therapeutic agent may be provided as separate component parts. A kit may include a plurality of containers, each container holding one or more unit dose of the compound. The containers may be adapted for the desired mode of administration, including, but not limited to tablets, gel capsules, sustained-release capsules, and the like for oral administration; depot products, pre-filled syringes, ampoules, vials, and the like for parenteral administration; and patches, medipads, creams, and the like for topical administration.

The concentration of active compound in the drug composition will depend on absorption, inactivation, and excretion rates of the active compound, the dosage schedule, and amount administered as well as other factors commonly considered by those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound can be formulated in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. Syrups can contain, in addition to the active compounds, sucrose as a sweetening agent and certain preservatives, dyes and colorings, and flavors.

The active materials can also be mixed with other active materials that do not impair the desired action, or with materials that supplement the desired action.

Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known in the art, for example, as described in U.S. Pat. No. 4,522,811.

The active compounds may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

Compounds may be administered enterally or parenterally. When administered orally, compounds can be administered in usual dosage forms for oral administration as is well known to those skilled in the art. These dosage forms include the usual solid unit dosage forms of tablets and capsules as well as liquid dosage forms such as solutions, suspensions, and elixirs. Solid dosage forms may be of the sustained release type so that the compounds can be administered only once or twice daily. In embodiments delivery systems can incorporate mesoporous materials such as the non-limiting examples of metal oxides (e.g., $Al_2O_3$) and amine functionalized mesoporurous silica (e.g., MCM-48) for sustained or delayed release of inhibitor molecules. The release profile and characteristics of such systems can be adjusted by modification of the material pore size and shape, overall structure, and surface chemistry [See, Kapoor, et al., *J. Phys. Chem. B.*, 114: 3117-3121; "Inhibition of a Protein Tyrosine Phosphatase Using Mesoporous Oxides."

The oral dosage forms are administered to the subject 1, 2, 3, or 4 times daily. In some embodiments, the compounds can be administered either three or fewer times, or once or twice daily. In some embodiments, the compounds are administered in oral dosage form. In some embodiments, the oral dosage form is designed so as to protect the compounds from the acidic environment of the stomach. Enteric coated tablets are well known to those skilled in the art. In addition, capsules filled with small spheres each coated to protect from the acidic stomach, are also well known to those skilled in the art.

As noted above, depending on whether asymmetric carbon atoms are present, the compounds can be present as mixtures of isomers, as racemates, or in the form of pure isomers.

Salts of compounds include the pharmaceutically acceptable or non-toxic salts. For synthetic and purification purposes it is also possible to use pharmaceutically unacceptable salts.

The composition can include an additional agent effective for the treatment of a disease or disorder associated with microbial infection, such as are commonly used in such treatment.

Further aspects provide methods of treating and/or preventing a disorder or disease associated with microbial infection such as, for example, sepsis, arthritis, pneumonia, osteomyelitis, endocarditis, toxic shock syndrome, and the like, in a subject in need of such treatment, wherein the method includes administering to the subject an effective amount of a compound, or salt thereof, identified by the methods described herein. In embodiments the methods can ameliorate the disease or disorder associated with microbial infection. In embodiments the methods can ameliorate the disease or disorder associated with MRSA infection. In embodiments the methods can delay or slow the development or progression of the disease or disorder associated with microbial infection. In embodiments the methods can delay or slow the development or progression of the disease or disorder associated with MRSA infection. In embodiments, the method treats the infection caused by the microbe such as, for example, S. aureus or MRSA. In embodiments, the method inhibits the biological activity of the microbe causing the infection such as, for example, S. aureus or MRSA. In embodiments the subject is human.

The methods of treatment employ therapeutically effective amounts: for oral administration from about 0.1 mg/day to about 1,000 mg/day; for parenteral, sublingual, intranasal, intrathecal administration from about 0.5 to about 100 mg/day; for depo administration and implants from about 0.5 mg/day to about 50 mg/day; for topical administration from about 0.5 mg/day to about 200 mg/day; for rectal administration from about 0.5 mg to about 500 mg.

Therapeutically effective amounts for oral administration can be from about 1 mg/day to about 100 mg/day, 1 mg/day to about 50 mg/day; and for parenteral administration from about 5 to about 50 mg daily.

Aspects provide a compound identified by the methods described herein for the preparation of a medicament for the treatment of a condition, disease, or disorder which is mediated by or related to the biological activity of S. aureus.

Aspects provide a medicament for the treatment of an S. aureus infection and/or one or more diseases or disorders related to S. aureus infection. Embodiments provide a medicament for the treatment of one or more respiratory infections. Embodiments provide a medicament for the treatment of one or more skin or soft tissue infections.

Embodiments provide a medicament for the treatment of sepsis. Embodiments provide a medicament for the treatment of arthritis. Embodiments provide a medicament for the treatment of pneumonia. Embodiments provide a medicament for the treatment of osteomyelitis. Embodiments provide a medicament for the treatment of endocarditis. Embodiments provide a medicament for the treatment of toxic shock syndrome.

Aspects also provide a method of inhibiting S. aureus biological activity that include contacting a S. aureus cell with a compound identified by one or more assays described herein effective to inhibit S. aureus biological activity. In some embodiments the method inhibits S. aureus biological activity by about three- to five-fold relative to normal activity. In various embodiments the methods inhibit S. aureus biological activity by about five-fold to about ten-fold, by about ten-fold to fifteen-fold, or by about fifteen-fold to about twenty-fold over normal activity. In embodiments the methods inhibit S. aureus biological activity completely (i.e., it kills the S. aureus cell). The S. aureus cell can be present in a host cell or host organism such as, for example, a mammalian cell or a mammal. In some embodiments the host organism is a human. In some embodiments the host cell is a human cell.

Methods of inhibiting S. aureus biological activity can be used to treat a subject that has a disease or a disorder related to S. aureus infection. In some embodiments, the subject demonstrates clinical signs of a disease or a disorder related to S. aureus infection. In some embodiments, the subject is diagnosed with a disease or a disorder related to S. aureus infection. In some embodiments the subject merely presents the clinical signs of S. aureus infection. In some embodiments the subject presents the clinical signs of S. aureus infection and the clinical signs of a disease or a disorder related to S. aureus infection.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each functions and/or operation within such block diagram, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of farms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., fiber optic cable, a waveguide, a wired communications link, a wireless communication link, etc.).

Those skilled in the art will recognize that it is common within the art to described device and/or processes in the fashion set forth herein, and thereafter use engineering practices to integrate such described devise and/or processes into data processing systems. That is, at least a portion of the devices and/or processes described herein can be integrated into a data processing system via a reasonable amount of experimentation. Those having skill in the art will recognize that typical data processing system generally includes one or more of a system unit housing, a video display device, a memory such as volatile and non-volatile memory, processors such as microprocessors and digital processors, computational entities such as operating systems, drivers graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

The foregoing summary is illustrative only and is not intended to be in any way limiting. In addition to the illustrative aspects, embodiments, and features described above, further aspects, embodiments, and features will become apparent by reference to the drawings and the following detailed description.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All reference, including but not limited to patents, patent applications, and non-patent literature are hereby incorporated by reference herein in their entirety.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The Examples that follow are merely illustrative of certain embodiments and are not to be taken as limiting.

EXAMPLES

Standard techniques and equipment were used in the following examples. In certain instances particular techniques and/or equipment are described for purposes of clarity.

Example 1

Cloning, Expression, and Purification of Recombinant DapE

The dapE gene (1.410 Kb; SEQ ID NO: 3) encoding DapE was PCR amplified from *Staphylococcus aureus* COL genomic DNA using 5'-GTT CGC TAG CAT GTG AAA AGA AAA AGT TCA A-3' (forward primer, SEQ ID NO: 4) and 5'-ACG CTC GAG TTA TTC CTC CAC GCA TAA TG-3' (reverse primer, SEQ ID NO: 5). Once amplified, the gene was subsequently cloned into the pET15b bacterial expression vector (NOVAGEN) between the NheI and XhoI restriction sites. To generate a site-directed mutant of DapE (R350A), the primers 5'-CTT TTC GGT ATC AAC TTA GCA TAC CCA GAA GGA TTT GAA-3' (forward primer, SEQ ID NO: 6) and 5'-TTC AAA TCC TTC TGG GTA TGC TAA GTT GAT ACC GAA AAG-3' (reverse primer, SEQ ID NO: 7) were used. The recombinant protein was expressed under the control of the T7 promoter in BL21(DE3) cells with a poly His-tag at the N-terminus. Isopropyl-β-D-1-thiogalactopyranoside (IPTG) was added ($C_f$=0.5 mM) to induce the protein expression when the cell density reached to an optical density of 0.6. Post-induction, the cells were grown at 23° C. for 8-10 hrs. Cells were harvested by centrifugation (10 min. @6,000 rpm). The cell pellet was resuspended in lysis buffer (50 mM Tris-HCl (pH 7.5), 250 mM NaCl, one complete EDTA-free protease inhibitor tablet (Roche)) and was lysed by sonication. The supernatant from the sonication was incubated with $Ni^{2+}$-NTA affinity beads (Sigma Aldrich Co.) for 1 hr at 4° C. The protein was eluted with a gradient of imidazole (conc. 5 mM-200 mM) in 50 mM Tris, 250 mM NaCl, pH 7.5. The protein was incubated with 10 mM EDTA solution on ice for 5 hrs and dialyzed overnight against 50 mM Tris-HCl, 200 mM NaCl, pH 7.5, 5 mM EDTA and glycerol (1.0%). In order to remove the EDTA, dialyzed protein was applied to a Sephacryl S-200 size-exclusion gel filtration column that was pre-equilibrated with 50 mM Tris, 200 mM NaCl (pH 7.5) and glycerol (1.0%). The R350A DapE mutant was purified by the same general protocol.

The $Mn^{2+}$ holo-protein was purified by the same procedure, except that 3 mM Tris-(2-carboxyethyl)phospine (TCEP) and 1.0 mM $MnCl_2$ were included in each of the purification buffers. Apo-DapE was prepared by incubating the purified protein with 10 mM EDTA on ice for about 5 hr with subsequent dialysis (for 24 hr) in a buffer containing 50 mM Tris-HCl, 200 mM NaCl, pH 7.5, and 10 mM EDTA. This dialysis was followed by another dialysis step for the same time and in the same buffer, but without EDTA.

Analytical Size-Exclusion Chromatography

Analytical gel filtration chromatography was performed using a Superdex S-200 gel filtration column on an UPC10 AKTA FPLC system (GE-Health Sciences), in order to characterize any variation in shape and association state (monomer, dimer, multimer, etc.) between the apo- and holo-forms of DapE protein. Purification buffers as described above were used as the running buffers (10 mM TCEP and 2 mM $MnCl_2$ included for holo-protein, 10 mM EDTA included for apo-protein). In separate experiments, aliquots (200 µL @1 mg/mL) of the proteins were applied to the column and passed through the column at a rate of 0.3 mL/min.

Crystallization and Data Collection

For both apo- and holo-proteins, initial screening for the crystallization conditions was performed using crystallization kits, silicon oil and paraffin oil (Hampton Research). The conditions were examined using both the hanging-drop method (protein conc. 5 mg/mL) and the sitting drop method under oil (protein conc. 10 mg/mL) at 293 K, where the drop (4 µL) contained 2 µL of protein solutions and 2 µL of precipitating reagent solution. Initial crystals of the apo-protein formed as thin rod/needle shaped micro-crystals in 0.2 M ammonium acetate and diamond-shaped micro-crystals in 1.8 M tri-ammonium citrate (pH 7.0). The conditions were modified in order to obtain diffraction-quality crystals (for apo-protein: 0.2 M ammonium acetate, 1.0 M Bis-Tris (pH 6.5) and 18.0% PEG6000; for holo-protein: 0.2 M magnesium (or alternatively, calcium) acetate tetrahydrate, 0.1 M sodium cacodylate (pH 6.8), and 22.0% PEG8000). Crystals of the R350A mutant were obtained using conditions containing 0.2 M ammonium sulfate, 0.2 M MES, pH 6.5 and 30.0% PEG Mono Methyl Ester 5000. The protein solution required the presence of an excess of $MnCl_2$ and TCEP in order to form good quality crystals. The crystals were flash frozen in liquid nitrogen using 10.0% glycerol as the cryoprotectant. All the data sets were processed using MOSFLM [see, Leslie, 1994] and scaled using SCALA (CCP4 suite). The data collection and processing statistics are reported in Table 1.

Structure Determination and Refinement

The structures were solved by molecular replacement using the program PHASER [see, Storoni et al., 2004]. Molecular Replacement (MR) strategy using the catalytic and lid domains of *Lacrobacillus delbruckii* pepV as independent search models led to a successful structure solution with a log likelihood gain of 300 using PHASER. The model was subsequently refined using Refmac5 [see, Murshudov et al., 1997] with multiple model building cycles using COOT [see, Cowtan et al., 2004]. TLS restraints were used to achieve convergence of refinement. As the crystal asymmetric unit contained two protein molecules, refinement was also carried out with NCS restraints until R-free reached a value of 32.0% after which NCS restraints were released and solvent molecules were added to obtain a final model with an Rcryst of 27.7% and an Rwork of 24.16%. For the cubic data set (holo-DapE), the phase information was obtained by MR with independent domains of the apo structure as the initial model. Refinement was carried out with solution from pepV intact model using Refmac5. TLS restraints were included in the refinement. Two $Mn^{2+}$ ions could be fit into the electron density map. The structures of the catalytic and lid domains determined for DapE in the open form was subsequently used as the initial search model in the MR calculations for the closed form, as well as for the structure of the R350A mutant.

The crystal structure data is provided herewith as a text file on a compact disk, which is incorporated herein by reference (referred to above). Structural data is also available through the Protein Data Bank (www.rcsb.org/pdb/home/home.do, PDB codes 3KHX (open form), 3KHZ (R350A mutant), and 3KI9 (closed form).

TABLE 1

| | Data Collection and Refinement | | |
|---|---|---|---|
| | Open form | R350A mutant | Closed form |
| | Data Collection | | |
| Wavelength (Å) | 0.98 | 1.5418 | 1.5418 |
| Resolution | 2.30 (2.42-2.30) | 2.50 (2.64-2.5) | 2.9 (3.06-2.9) |

TABLE 1-continued

| | Data Collection and Refinement | | |
|---|---|---|---|
| | Open form | R350A mutant | Closed form |
| Space Group | $P2_1$ | $P2_1$ | I23 |
| Unit cell dimensions | a = 64.80 Å | a = 64.75 Å | a = b = c = 158.15 Å |
| | b = 134.15 Å | b = 133.52 Å | |
| | c = 68.28 Å, | c = 67.71 Å, | |
| | β = 94.52° | β = 95.59° | |
| # observations | 185172 (27397) | 337344 (47881) | 116012 (16641) |
| # unique observations | 51315 (7488) | 39597 (5730) | 14758.0 (2141) |
| Mean I/σ(I) | 14.8 (3.2) | 20.9 (4.9) | 14.2 (3.6) |
| Multiplicity | 3.6 (3.7) | 8.5 (8.4) | 7.9 (7.8) |
| Completeness | 99.4 (99.6) | 100.0 (100.0) | 100.0 (100.0) |
| $R_{merge}$ (%) | 7.1 (35.4) | 6.8 (41.4) | 10.8 (56.3) |
| | Refinement | | |
| Rwork (%) | 24.16 | 20.77 | 20.21 |
| Rfree (%) | 27.70 | 26.90 | 26.26 |
| | Model Statistics | | |
| Number of Residues | 938 | 938 | 469 |
| Number of water molecules | 438 | 119 | 45 |
| RMSD bond length (Å) | 0.009 | 0.011 | 0.005 |
| RMSD bond-angle | 1.246 | 1.350 | 0.937 |

Measurement of Activity (Regeneration by Cd-Ninhydrin)

The apo-form of DapE was incubated with 2.0 mM $MnCl_2$ in the presence and absence of 3.0 mM TCEP as reducing agent prior to the assay. In this colorimetric assay, various concentrations of the Phe-Val dipeptide substrate (from 0.125 mM to 4.0 mM) were added to the reaction mixture containing 25 mM Tris buffer (pH 7.5) and 2.0 mM $MnCl_2$. Microcentrifuge tubes containing different concentrations of the Phe-Val dipeptide substrates were pre-incubated at 37° C. for 10 min. The reactions were initiated by adding 5.0 µL of the enzyme into a total reaction volume of 100 µL. The reaction mixture was further incubated at 37° C. in a rotating shaker incubator for 30 min. The dipeptidase reaction was stopped by adding Cd-Ninhydrin reagent. The microcentrifuge tubes were heated at 84° C. for 10 min. in order to develop the color. The intensity of the color was measured by monitoring the $A_{507}$. This was examined by reference to a standard plot obtained using calibrated amounts of Phe and Val amino acids. The kinetic parameters were calculated by a non-linear least squares fit of the data using the Origin software package. TCEP (3.0 mM) was included in the assay buffer for measuring the dipeptidase activity under reducing conditions.

Qualitative hydrolytic activity for a number of dipeptide substrates were examined and are summarized in Table 2. The dipeptidase activity of DapE was screened using a TLC assay. For the assay, 10 µL of dipeptide substrate (5.0 mg/mL) was incubated at 37° C. for 30 min with 2 µg of DapE in 50 mM Tris-HCl buffer (pH 7.5). The hydrolysis was monitored by running 5 µL of each of the reaction mixtures on silica coated TLC plates using ethanol:acetic acid (90:10) solvent mixture as the mobile phase. The resulting spots were visualized by spraying 1.0% Ninhydrin in acetone and developing the plates.

TABLE 2

| S. aureus DapE Qualitative Dipeptidase Activity | |
|---|---|
| Dipeptide | Activity |
| Gly-Lys | + |
| Ala-Ser | + |
| His-Leu | + |
| Asp-Lys | + |
| Gly-Ser | + |
| Lys-Phe | ++ |
| Lys-Leu | ++ |
| Ser-His | ++ |
| Phe-Val | +++ |
| Arg-Ala | +++ |
| Arg-Val | +++ |
| Arg-Leu | +++ |
| Arg-Ile | +++ |

+ = Mild hydrolytic activity

++ = Moderate hydrolytic activity

+++ = High hydrolytic activity

Nitrocefin Assay

The kinetic parameters for β-lactamase activity of S. aureus DapE were calculated by monitoring the hydrolysis of chromogenic cephalosporin Nitrocefin. Nitrocefin undergoes a change in color from yellow (λmax ~390 nm) to red (λmax ~486 nm) upon hydrolysis of the amide bond in the β-lactam ring. Various concentrations of Nitrocefin ranging from 0.03125 mM to 1.0 mM were included in the reaction mixture containing 50 mM phosphate buffer (pH 7.5). The reaction was initiated by adding 5 µL (10 µM) of various dilutions DapE and the hydrolysis was monitored by following the increase in absorbance at 486 nm. A molar extinction coefficient of 20500 $M^{-1}cm^{-1}$ was used to calculate the activity. The kinetic parameters were calculated by non-linear least squares fit of the data to the Michaelis-Menten equation using Origin software. A summary of the results are presented in Table 3.

TABLE 3

S. aureus DapE Summary of Kinetic Peptidase Activity

| Protein | $K_m$ (mM) | $V_{max}$ (μmols mnt$^{-1}$ mg$^{-1}$) | $K_{cat}$ (mnt$^{-1}$) | Relative activity (%) |
|---|---|---|---|---|
| holo-DapE | 0.67 ± 0.10 | 1.44 ± 0.70 | 0.08 ± 0.005 | 0.72 |
| holo-DapE + Mn$^{2+}$ | 1.15 ± 0.12 | 60 ± 3 | 3.33 ± 0.16 | 0.57 |
| holo-DapE + Mn$^{2+}$ + TCEP | 1.1 ± 0.10 | 200 ± 7 | 11.11 ± 0.38 | 100.0 |
| apo-DapE + Mn$^{2+}$ | 0.52 ± 1.24 | 5.96 ± 0.6 | 0.33 ± 0.035 | 2.98 |
| apo-DapE + Mn$^{2+}$ + TCEP | 1.64 ± 0.22 | 169.65 ± 10 | 9.425 ± 0.55 | 84.50 |

Analysis of Sulfhydryl Groups (DTNB and Mass Spectrometry)

The apo protein (5 μM) was denatured by incubation (1 hr) at room temperature in 7 M Guanidinium hydrochloride. The free thiol content was determined by adding 1000× molar excess of DTNB reagent and monitoring the absorbance at 412 nm. An extinction coefficient of 13700 M$^{-1}$cm$^{-1}$ for thionitrobenzoate (TNB$^{2-}$) anion was used to calculate the number of free sulfhydryl groups under denaturing conditions. In order to determine the total number of sulfhydryl groups in the reduced apo-protein, 5 μM of apo-protein was first incubated with 10 mM of TCEP at room temperature (4 hrs) and analyzed using the above-described procedure. For analysis by mass spec, DTNB labeled proteins from the above reaction mixture were further passed through a desalting column equilibrated with 10 mM ammonium bicarbonate buffer to remove excess DTNB and guanidinium hydrochloride, and analyzed by LC-ESI mass spectrometry.

Isothermal Titration Calorimetry of Mn$^{2+}$ Binding to DapE

All titration experiments were carried out in a VP-ITC MicroCalorimeter (MicroCal, Inc.) at 25° C. The apo-protein used in the ITC binding experiments was dialyzed against 25 mM Hepes, 200 mM NaCl (pH 7.5). The ligand (MnCl2) for titration was prepared as a solution in the final dialysis buffer. In this experiment, the sample cell (1.4 mL) was filled with 35 μM DapE and the ITC syringe ($V_{total}$ 298 μL) was loaded with 5 mM of the MnCl2 solution. Titrations were performed by stepwise addition of 5 μL it ligand solution into the sample cell. A time interval of 108 s between successive injections and a stirring speed of 307 rpm was maintained throughout the titration. The enthalpic, $K_b$, and stoichiometric values of the ligand binding were determined by non-linear least squares fit of the data using Origin 7.0 software. The change in entropy (ΔS) was obtained using the equation ΔG=ΔH$_b$=TΔS, where ΔG=−RT ln$K_b$.

The invention claimed is:

1. A method for identifying a candidate inhibitor that preferentially binds to *Staphylococcus aureus* N-Succinyl-L,L-DAP Desuccinylase (DapE) or a homologue or active fragment thereof in the open conformation, comprising:

obtaining the structure coordinates of amino acids of DapE or homologue or active fragment thereof wherein the structure coordinates include the binding site of DapE or homologue or active fragment thereof comprises amino acid residues Glu-150, Ser-151, His-180, Gly-181, Glu-182, Lys-183, Arg-214, Asn-216, His-269, Arg-350, His-384, Tyr-385, Val-386, Asp-387, Lys-388, Thr-412, Gly-416, and His-440 of SEQ ID NO:2;

generating a three-dimensional model of DapE or homologue or active fragment thereof using the structure coordinates of the amino acids from DapE in closed and open conformations, wherein the model comprises a root mean square deviation from backbone atoms of said amino acids of not more than ±1.0 Å;

determining the binding site of DapE or homologue thereof in the closed confirmation from the three-dimensional model, and separately determining the binding site of DapE or homologue thereof in the open confirmation; and performing a computer fitting analysis to identify the candidate inhibitor that interacts with the binding site of DapE in the open confirmation but does not interact with the binding site of DapE in the closed configuration, and prevents interaction of the DapE lid domain with the DapE catalytic domain, wherein the interface of the catalytic domain and the lid domain comprises amino acid residues Glu-150, Ser-151, His-180, Gly-181, Glu-182, Lys-183, Arg-214, Asn-216, His-269, Arg-350, His-384, Tyr-385, Val-386, Asp-387, Lys-388, Thr-412, Gly-416, and His-440 of SEQ ID NO:2.

2. The method of claim 1, wherein the *S. aureus* DapE or active fragment thereof is from a methicillin resistant *S. aureus* (MRSA) strain.

3. The method for identifying a candidate inhibitor of claim 1, further comprising contacting the identified candidate inhibitor with DapE or homologue or active fragment thereof under conditions that allow for determination the effect of the inhibitor on *S. aureus* biological activity.

4. The method of claim 1, wherein the fitting analysis of the interaction between the candidate inhibitor and the binding site predicts that the inhibitor will bind at the interface between the catalytic domain and the lid domain.

5. The method of claim 1, wherein said structure coordinates of amino acids of DapE are as found in Table S1 and Table S2.

6. A method for identifying a candidate inhibitor that preferentially binds to *Staphylococcus aureus* N-Succinyl-L,L-DAP Desuccinylase (DapE) or a homologue or active fragment thereof in the open conformation, comprising:

obtaining the structure coordinates of amino acids of DapE or homologue or active fragment thereof under closed (reducing) and open (oxidizing) conditions, generating a three-dimensional model of DapE or homologue or active fragment thereof at the root mean square deviation from backbone atoms of said amino acids of not more than ±1.0 Å, using the structure coordinates of the amino acids from DapE in closed and open conformations, determining a binding site of DapE or homologue thereof in the closed confirmation from the three-dimensional model, wherein DapE lacks a disulfide bond between Cys-155 and Cys-178, separately determining the binding site of DapE or homologue thereof in the open confirmation, wherein DapE possess a disulfide bond between Cys-155 and Cys-178 and the lid domain is rotated by about 71° and performing a computer fitting analysis to identify the candidate inhibitor that interacts with DapE in the open confirmation but does not interact with the binding site of DapE in the closed configuration, and prevents rotation of the DapE lid domain towards the DapE catalytic domain, wherein the interface of the catalytic domain and the lid domain comprises amino acid residues Glu-150, Ser-151, His-180, Gly-181, Glu-182, Lys-183, Arg-214, Asn-216, His-269, Arg-350, His-384, Tyr-385, Val-386, Asp-387, Lys-388, Thr-412, Gly-416, and His-440 of SEQ ID NO:2.

7. The method for identifying a candidate inhibitor of claim 6, further comprising contacting the identified candidate inhibitor with DapE or homologue or active fragment thereof under conditions that allow for determination the effect of the inhibitor on *S. aureus* biological activity.

8. The method of claim 6, wherein said structure coordinates of amino acids of DapE are as found in Table S1 and Table S2.

* * * * *

UNITED STATES PATENT AND TRADEMARK OFFICE
CERTIFICATE OF CORRECTION

PATENT NO. : 8,639,486 B2
APPLICATION NO. : 12/840925
DATED : January 28, 2014
INVENTOR(S) : Tavarekere et al.

It is certified that error appears in the above-identified patent and that said Letters Patent is hereby corrected as shown below:

On the Title Page

Item (75), under "Inventors", in Column 1, Line 1, delete "Girish S" and insert -- Girish S. --, therefor.

In the Drawings

In Fig. 2B, Sheet 2 of 16, delete "Cataytic domain" and insert -- Catalytic domain --, therefor.

In the Specification

In Column 6, Line 11, delete "shows optional" and insert -- shows an optional --, therefor.

In Column 6, Line 13, delete "shows optional" and insert -- shows an optional --, therefor.

In Column 10, Line 41, delete "microliter" and insert -- microtiter --, therefor.

In Column 13, Line 57, delete "Or" and insert -- or --, therefor.

In Column 22, Line 57, delete "data;" and insert -- data. --, therefor.

In Column 23, Line 10, delete "interfaces (660)" and insert -- interfaces (670) --, therefor.

In Column 26, Lines 60-61, delete "mesopourous" and insert -- mesoporous --, therefor.

In Column 28, Line 54, delete "and or" and insert -- and/or --, therefor.

In Column 28, Line 59, delete "farms," and insert -- forms, --, therefor.

In Column 31, Line 50, delete "MnCl2" and insert -- $MnCl_2$ --, therefor.

Signed and Sealed this
Twentieth Day of May, 2014

Michelle K. Lee
*Deputy Director of the United States Patent and Trademark Office*

CERTIFICATE OF CORRECTION (continued)
U.S. Pat. No. 8,639,486 B2

In Column 32, Line 55, delete "(www.rcsb.org/pdb/home/home.do," and insert -- (www.rcsb.org/pdb/home/home.do), --, therefor.

In Column 36, Line 17, delete "(MnCl2)" and insert -- ($MnCl_2$) --, therefor.

In Column 36, Line 22, delete "MnCl2" and insert -- $MnCl_2$ --, therefor.

In the Claims

In Column 44, Line 18, in Claim 6, delete "about 71° and" and insert -- about 71°, and --, therefor.

```
SEQUENCE LISTING

<160> NUMBER OF SEQ ID NOS: 7

<210> SEQ ID NO 1
<211> LENGTH: 295
<212> TYPE: PRT
<213> ORGANISM: Staphylococcus aureus

<400> SEQUENCE: 1

Met Thr His Leu Phe Glu Gly Val Gly Val Ala Leu Thr Thr Pro Phe
1               5                   10                  15

Thr Asn Asn Lys Val Asn Ile Glu Ala Leu Lys Thr His Val Asn Phe
            20                  25                  30

Leu Leu Glu Asn Asn Ala Gln Ala Ile Ile Val Asn Gly Thr Thr Ala
        35                  40                  45

Glu Ser Pro Thr Leu Thr Thr Asp Glu Lys Glu Arg Ile Leu Lys Thr
    50                  55                  60

Val Ile Asp Leu Val Asp Lys Arg Val Pro Val Ile Ala Gly Thr Gly
65                  70                  75                  80

Thr Asn Asp Thr Glu Lys Ser Ile Gln Ala Ser Ile Gln Ala Lys Ala
                85                  90                  95

Leu Gly Ala Asp Ala Ile Met Leu Ile Thr Pro Tyr Tyr Asn Lys Thr
            100                 105                 110

Asn Gln Arg Gly Leu Val Lys His Phe Glu Ala Ile Ala Asp Ala Val
        115                 120                 125

Lys Leu Pro Val Val Leu Tyr Asn Val Pro Ser Arg Thr Asn Met Thr
    130                 135                 140

Ile Glu Pro Glu Thr Val Glu Ile Leu Ser Gln His Pro Tyr Ile Val
145                 150                 155                 160
```

```
Ala Leu Lys Asp Ala Thr Asn Asp Phe Glu Tyr Leu Glu Glu Val Lys
            165                 170                 175

Lys Arg Ile Asp Thr Asn Ser Phe Ala Leu Tyr Ser Gly Asn Asp Asp
        180                 185                 190

Asn Val Val Glu Tyr Tyr Gln Arg Gly Gly Gln Gly Val Ile Ser Val
            195                 200                 205

Ile Ala Asn Val Ile Pro Lys Glu Phe Gln Ala Leu Tyr Asp Ala Gln
        210                 215                 220

Gln Ser Gly Leu Asp Ile Gln Asp Gln Phe Lys Pro Ile Gly Thr Leu
225                 230                 235                 240

Leu Ser Ala Leu Ser Val Asp Ile Asn Pro Ile Pro Ile Lys Ala Leu
            245                 250                 255

Thr Ser Tyr Leu Gly Phe Gly Asn Tyr Glu Leu Arg Leu Pro Leu Val
        260                 265                 270

Ser Leu Glu Asp Thr Asp Thr Lys Val Leu Arg Glu Thr Tyr Asp Thr
        275                 280                 285

Phe Lys Ala Gly Glu Asn Glu
        290                 295

<210> SEQ ID NO 2
<211> LENGTH: 469
<212> TYPE: PRT
<213> ORGANISM: Staphylococcus aureus

<400> SEQUENCE: 2

Met Trp Lys Glu Lys Val Gln Gln Tyr Glu Asp Gln Ile Ile Asn Asp
1               5                   10                  15

Leu Lys Gly Leu Leu Ala Ile Glu Ser Val Arg Asp Asp Ala Lys Ala
            20                  25                  30

Ser Glu Asp Ala Pro Val Gly Pro Gly Pro Arg Lys Ala Leu Asp Tyr
        35                  40                  45

Met Tyr Glu Ile Ala His Arg Asp Gly Phe Thr Thr His Asp Val Asp
    50                  55                  60

His Ile Ala Gly Arg Ile Glu Ala Gly Lys Gly Asn Asp Val Leu Gly
65                  70                  75                  80

Ile Leu Cys His Val Asp Val Val Pro Ala Gly Asp Gly Trp Asp Ser
            85                  90                  95

Asn Pro Phe Glu Pro Val Val Thr Glu Asp Ala Ile Ile Ala Arg Gly
        100                 105                 110

Thr Leu Asp Asp Lys Gly Pro Thr Ile Ala Ala Tyr Tyr Ala Ile Lys
        115                 120                 125

Ile Leu Glu Asp Met Asn Val Asp Trp Lys Lys Arg Ile His Met Ile
    130                 135                 140

Ile Gly Thr Asp Glu Glu Ser Asp Trp Lys Cys Thr Asp Arg Tyr Phe
145                 150                 155                 160

Lys Thr Glu Glu Met Pro Thr Leu Gly Phe Ala Pro Asp Ala Glu Phe
            165                 170                 175

Pro Cys Ile His Gly Glu Lys Gly Ile Thr Thr Phe Asp Leu Val Gln
        180                 185                 190

Asn Lys Leu Thr Glu Asp Gln Asp Glu Pro Asp Tyr Glu Leu Ile Thr
        195                 200                 205

Phe Lys Ser Gly Glu Arg Tyr Asn Met Val Pro Asp His Ala Glu Ala
    210                 215                 220

Arg Val Leu Val Lys Glu Asn Met Thr Asp Val Ile Gln Asp Phe Glu
225                 230                 235                 240
```

```
Tyr Phe Leu Glu Gln Asn His Leu Gln Gly Asp Ser Thr Val Asp Ser
                245                 250                 255

Gly Ile Leu Val Leu Thr Val Glu Gly Lys Ala Val His Gly Met Asp
            260                 265                 270

Pro Ser Ile Gly Val Asn Ala Gly Leu Tyr Leu Leu Lys Phe Leu Ala
        275                 280                 285

Ser Leu Asn Leu Asp Asn Asn Ala Gln Ala Phe Val Ala Phe Ser Asn
    290                 295                 300

Arg Tyr Leu Phe Asn Ser Asp Phe Gly Glu Lys Met Gly Met Lys Phe
305                 310                 315                 320

His Thr Asp Val Met Gly Asp Val Thr Thr Asn Ile Gly Val Ile Thr
                325                 330                 335

Tyr Asp Asn Glu Asn Ala Gly Leu Phe Gly Ile Asn Leu Arg Tyr Pro
            340                 345                 350

Glu Gly Phe Glu Phe Glu Lys Ala Met Asp Arg Phe Ala Asn Glu Ile
        355                 360                 365

Gln Gln Tyr Gly Phe Glu Val Lys Leu Gly Lys Val Gln Pro Pro His
    370                 375                 380

Tyr Val Asp Lys Asn Asp Pro Phe Val Gln Lys Leu Val Thr Ala Tyr
385                 390                 395                 400

Arg Asn Gln Thr Asn Asp Met Thr Glu Pro Tyr Thr Ile Gly Gly Gly
                405                 410                 415

Thr Tyr Ala Arg Asn Leu Asp Lys Gly Val Ala Phe Gly Ala Met Phe
            420                 425                 430

Ser Asp Ser Glu Asp Leu Met His Gln Lys Asn Glu Tyr Ile Thr Lys
        435                 440                 445

Lys Gln Leu Phe Asn Ala Thr Ser Ile Tyr Leu Glu Ala Ile Tyr Ser
    450                 455                 460

Leu Cys Val Glu Glu
465

<210> SEQ ID NO 3
<211> LENGTH: 1410
<212> TYPE: DNA
<213> ORGANISM: Staphylococcus aureus

<400> SEQUENCE: 3
atgtggaaag aaaaagttca acaatacgaa gatcaaatca ttaatgactt aaaaggatta      60
ttagcaattg aaagtgtgag agatgatgca aaagcatcag aagacgcacc agttggtcca     120
ggtcctcgta aggcattaga ctacatgtat gaaattgcac atagagatgg atttacaaca     180
catgatgtgg atcatattgc aggaagaatt gaggcaggta aggaaatga cgtattaggt     240 atcttatgtc atgttgacgt tgttcctgct ggtgatggat gggatagtaa tccgttcgag     300
ccggttgtaa cagaagatgc tatcatagct agaggtacac ttgatgacaa aggtccaaca     360
attgctgctt attatgcaat taagatatta gaagatatga atgtggattg aagaaacgt     420 attcatatga ttattggtac ggatgaagaa tctgattgga atgtacgga tcgctatttt     480 aaaacagaag aaatgccaac attaggtttt gcaccagatg cagaatttcc atgtattcat     540
ggtgaaaaag gcattacaac atttgattta gttcaaaata aacttactga agatcaagat     600
gaacctgatt atgaattaat aacttttaaa tctggtgaac gttacaacat ggtacctgat     660
catgcagaag caagagtgct tgttaaagaa aatatgacag atgttattca agactttgag     720 tacttttag aacaaaatca tttcaaggt gatagtactt tgatagtgg cattctagtt     780 ttaacagttg aaggtaaagc ggttcatggt atggatccat ctatcggtgt gaatgcgggt     840
```

```
ctttacttac taaaattctt agcatcatta aatcttgata ataatgcaca agcgtttgta      900
gcatttagta atcgctactt atttaattca gattttggtg aaaagatggg aatgaaattc      960
catacagatg tcatgggtga cgtgacaact aacattggtg ttattacata tgataatgaa     1020
aacgcaggtc ttttcggtat caacttacgc tacccagaag gatttgaatt tgaaaaagct     1080
atggatcgtt ttgcaaatga gattcaacaa tatggctttg aagtgaaatt aggtaaagtc     1140
caaccaccac attatgttga taaaaatgat cctttgtac aaaagttagt tactgcatat      1200
agaaatcaaa caaatgatat gactgaacct tatactatag gtggcggtac ttatgcgaga     1260
aacttagaca agggtgtagc atttggcgca atgtttagtg attctgaaga tttaatgcat     1320
cagaaaaatg aatatatcac taaaaaacag ttatttaacg caactagtat ttacttagaa     1380
gcaatttatt cattatgcgt ggaggaataa                                      1410
```

```
<210> SEQ ID NO 4
<211> LENGTH: 31
<212> TYPE: DNA
<213> ORGANISM: Artificial Sequence
<220> FEATURE:
<223> OTHER INFORMATION: Forward primer

<400> SEQUENCE: 4
gttcgctagc atgtggaaag aaaaagttca a                                      31

<210> SEQ ID NO 5
<211> LENGTH: 29
<212> TYPE: DNA
<213> ORGANISM: Artificial Sequence
<220> FEATURE:
<223> OTHER INFORMATION: Reverse primer

<400> SEQUENCE: 5
acgctcgagt tattcctcca cgcataatg                                         29

<210> SEQ ID NO 6
<211> LENGTH: 39
<212> TYPE: DNA
<213> ORGANISM: Artificial Sequence
<220> FEATURE:
<223> OTHER INFORMATION: Forward primer

<400> SEQUENCE: 6
cttttcggta tcaacttagc atacccagaa ggatttgaa                              39

<210> SEQ ID NO 7
<211> LENGTH: 39
<212> TYPE: DNA
<213> ORGANISM: Artificial Sequence
<220> FEATURE:
<223> OTHER INFORMATION: Reverse primer

<400> SEQUENCE: 7
ttcaaatcct tctgggtatg ctaagttgat accgaaaag                              39
```